(12) United States Patent
Muñoz Risueño

(10) Patent No.: US 11,337,984 B2
(45) Date of Patent: *May 24, 2022

(54) METHODS FOR TREATING, DIAGNOSING AND PROGNOSING A HAEMATOLOGICAL MALIGNANCY

(71) Applicant: Institut de Recerca Contra La Leucèmia Josep Carreras, Barcelona (ES)

(72) Inventor: Ruth Muñoz Risueño, Barcelona (ES)

(73) Assignee: Institut de Recerca Contra la Leucémia Josep Carreras, Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/216,701

(22) Filed: Dec. 11, 2018

(65) Prior Publication Data
US 2019/0343843 A1 Nov. 14, 2019

Related U.S. Application Data

(63) Continuation of application No. 15/322,012, filed as application No. PCT/EP2015/064571 on Jun. 26, 2015, now Pat. No. 10,195,207.

(30) Foreign Application Priority Data

Jun. 27, 2014 (EP) .................................... 14382249

(51) Int. Cl.
| | | |
|---|---|---|
| *A61K 31/55* | (2006.01) | |
| *G01N 33/574* | (2006.01) | |
| *G01N 33/94* | (2006.01) | |
| *A61K 31/473* | (2006.01) | |
| *A61K 31/495* | (2006.01) | |
| *A61P 35/02* | (2006.01) | |
| *G01N 33/50* | (2006.01) | |

(52) U.S. Cl.
CPC ............ *A61K 31/55* (2013.01); *A61K 31/473* (2013.01); *A61K 31/495* (2013.01); *A61P 35/02* (2018.01); *G01N 33/5091* (2013.01); *G01N 33/57426* (2013.01); *G01N 33/942* (2013.01); *G01N 2800/52* (2013.01)

(58) Field of Classification Search
CPC ..................................................... A61K 31/55
USPC ........................................................ 514/252
See application file for complete search history.

(56) References Cited

U.S. PATENT DOCUMENTS

| | | |
|---|---|---|
| 3,155,669 A | 11/1964 | Janssen et al. |
| 3,155,670 A | 11/1964 | Janssen et al. |
| 3,337,628 A | 8/1967 | Crowther et al. |
| 3,471,515 A | 10/1969 | Troxler et al. |
| 3,466,325 A | 11/1969 | Brandstrom et al. |
| 3,551,493 A | 12/1970 | Ruschig et al. |
| 3,960,891 A | 6/1976 | Malen et al. |
| 2016/0287577 A1 | 10/2016 | Rolls et al. |

FOREIGN PATENT DOCUMENTS

| | | | |
|---|---|---|---|
| EP | 0 687 472 A2 | 10/1994 | |
| WO | 2003/063866 A1 | * 8/2003 | |
| WO | WO 03/063866 A1 | 8/2003 | |
| WO | WO 2004/072651 A2 | 8/2004 | |
| WO | WO 2008/098351 A1 | 8/2008 | |
| WO | WO 2008/145754 A2 | 12/2008 | |
| WO | WO 2010/135468 A1 | 11/2010 | |

OTHER PUBLICATIONS

Sibella-Arguelles, C.R. Acad. Sci. III, (2000), vol. 324(4), pp. 365-372, Elsevier, Netherlands.*
Mossner et al., Brain, Behav. Immun. (1998), vol. 12, pp. 249-271.*
Kondo et al., J. Pharmacobio-Dyn., (1990) 13, pp. 426-431.*
Hajighasemi, Fatemeh, and Mirshafiey, Abbas., "In Vitro Sensitivity of Leukemia Cells to Propranolol," *J Clin Med Res* I(3): 144-149, Elmer Press, Canada (2009).
Kahn, A.R., et al., "Identification of Small Molecules Selectively Targeting Leukemic Stem Cells within their Stromal Niche," *Blood* 120:41, American Society of Hematology, United States (2012).
Kahn, A.R., et al., "Selective Targeting of Leukemic Over Normal Stem Cells by the Serotonin Receptor Antagonist SB-216641," *Blood* 118:1884, American Society of Hematology, United States (2011).
Kondso, Yoshikazu, et al.,"Supression of Tumor Cell growth and Mitogen Response by Aporphine Alkaloids, Dicentrine, Glaucine, Corydine, and Apomorphine," *J. Pharmacabio-Dyn* 13:426-431, Elsevier, Netherlands (1989).
Moreau, J.-L., et al., "Behavioral Profile of the $5HT_{1a}$ Receptor Antagonist (S)-UH-301 in Rodents and Monkeys," *Brain Research Bulletin* 29:901-904, Pergamon Press Ltd., United States (1992).
Sibella-Arguelles, Carla, "The proliferation of Human T lymphoblastic cells induced by $5-HT_{1b}$ receptors activation is regulated by 5-HT-moduline," *C R Acad Sci III* 324(4): 365-372, Elsevier, Netherlands (2000).

(Continued)

*Primary Examiner* — Taofiq A Solola
(74) *Attorney, Agent, or Firm* — Sterne, Kessler, Goldstein & Fox P.L.L.C.

(57) ABSTRACT

The invention relates to a serotonin receptor (5-HTR) inhibitor selected from the group consisting of a type 1 5-HTR inhibitor and a type 2 5-HTR inhibitor for use in the prevention and/or treatment of a haematological malignancy. Additionally, the invention relates to in vitro methods for the identification or isolation of a malignant cell from a haematological malignancy or for diagnosing a haematological malignancy based on detecting the expression of type 1 5-HTR and/or type 2 5-HTR. Furthermore, the invention relates to in vitro methods for determining the prognosis, for monitoring the effect of a therapy or for designing a customized therapy in a subject suffering from a haematological malignancy based on determining the levels of type 1 5-HTR and or type 2 5-HTR.

1 Claim, 16 Drawing Sheets

(56) References Cited

OTHER PUBLICATIONS

Reikvam, Hakon, et al., "The Possible Diagnostic and Prognostic Use of Systemic Chemokine Profiles in Clinical Medicine—The Experience in Acute Myeloid Leukemia from Disease Development and Diagnosis via Conventional Chemotherapy to Allogeneic Stem Cell Transplantation," *Toxins* 5:336-362, Avens Publishing Group, India (2013).

Xia, Z., et al., "The Antidepressants Imipramine, Clomipramine, and Citaloprame Induce Apoptosis in Human Acute Myeloid Leukemia HL-60 Cells via Caspase-3 Activation," *J. Biochem Molecular Toxicology* 13 (6):338-348, Wiley Online Library, United States (1999).

International Search Report for International Application No. EP2015/064571, European Patent Office, Netherlands, dated Dec. 30, 2015, 4 pages.

Written Opinion for International Application No. PCT/EP2015/064571, European Patent Office, Netherlands, dated Dec. 30, 2015, 8 pages.

Lissoni, P.; et al., "Psychooncology and Cancer Progression-Related Alterations of Pleasure-Associated Neurochemical System: Abnormal Neuroendocrine Response to Apomorphine in Advanced Cancer Patients," Neuroendocrinology Letters 24:50-3, Maghira & Maas Publications, Luxembourg (2003).

Meredith; E.J., et al., "Dopamine targets cycling B cells independent of receptors/transporter for oxidative attack: implications for non-Hodgkin's Lymphoma," Proc. Natl. Acad. Sci. 103(36):13485-90, National Academy of Sciences, United States (2006).

Matto; V., et al., "Apomorphine-induced upregulation of serotonin 5-HT2A receptors in male rats is independent from development of aggressive behavior," Journal of Physiology and Pharmacology 50(2):335-344, (1999).

Pruus; K et al., "5-HT1a Receptor Agonists Buspirone and Gepirone Attenuate Apomorphine-induced Aggressive Behavior in Adult Male Wistar Rats," Journal of Physiology and Pharmacology 51(4): 833-46, Polish Physiological Society, Poland (2000).

Stegmaier; K. et al., "Gene expression-based high-throughput screening (GE-HTS) and application to leukemia differentiation," Nat. Genet 36(3): 257-63, Nature Publishing Group (2004).

Ribarič; R., "The Pharmacological Properties and Therapeutic Use of Apomorphine," Molecules, 17: 5289-309, MDPI, Switzerland (2000).

* cited by examiner

B

A

B

METHODS FOR TREATING, DIAGNOSING AND PROGNOSING A HAEMATOLOGICAL MALIGNANCY

CROSS-REFERENCE TO RELATED APPLICATIONS

This application is a continuation of U.S. application Ser. No. 15/322,012 with a 371(c) date of Dec. 23, 2016, which is the national phase application of International Application No. PCT/EP2015/064571, filed Jun. 26, 2015, which claims the benefit of European Patent Application No. 14382249.2, filed Jun. 27, 2014, all of which are herein incorporated by reference in their entireties.

TECHNICAL FIELD OF THE INVENTION

The invention is related to the field of treatment, diagnostic and prognostic methods.

BACKGROUND OF THE INVENTION

Haematologic or haematopoietic malignancies are cancers of the blood or bone marrow, including leukaemia and lymphoma. Leukaemia is characterized by the uncontrolled accumulation of blood cells, which is categorized into four types: acute lymphocytic leukaemia (ALL), acute myelogenous leukaemia (AML), chronic lymphocytic leukaemia (CLL), and chronic myelogenous leukaemia (CML).

Acute myeloid leukaemia (AML), also referred to as non-lymphoid, myeloblastic, granulocytic or myelocytic leukaemia, affects various white blood cells including granulocytes and monocytes. Acute leukaemia is a rapidly progressing disease that results in the accumulation of immature, functionless cells in the marrow and blood; the marrow often stops producing enough normal red cells, white cells and platelets and leukaemic cells spread to the liver, spleen, lymph nodes, central nervous system, kidneys and gonads. Consequently, an AML patient can develop one or more symptoms of AML such as, for example, anemia, fatigue, flu-like symptoms, bone pain, loss of appetite, weight loss, bruising easily, bleeding, and susceptibility to infection.

More than one quarter of a million adults throughout the world are diagnosed annually with acute myeloid leukaemia (AML). Despite considerable progress during the past 3 decades in the therapy of AML, two-thirds of young adults and 90% of older adults still die of their disease.

The experience from patients with haematological malignancies, and especially patients with AML, suggests that systemic plasma/serum cytokine profiles can be useful, both as a diagnostic tool and for prognostication of patients. However, cytokines/chemokines are released by a wide range of cells and are involved in a wide range of biological processes; the altered levels may therefore mainly reflect the strength and nature of the biological processes, and the optimal clinical use of chemokine/cytokine analyses may therefore require combination with organ-specific biomarkers. Chemokine levels are also altered by clinical procedures, therapeutic interventions and the general status of the patients (Reikvam H. et al., Toxins (Basel). February 2013; 5(2): 336-362). Thus, novel diagnostic and prognostic methods are necessary to establish an optimal assessment and management for haematological malignancies.

Current treatments for AML may involve chemotherapy, radiotherapy, immunotherapy, blood transfusions, and bone marrow transplants. The mainstay of initial treatment, cytosine arabinoside (ara-C) combined with an anthracycline, was developed nearly 40 years ago and remains the worldwide standard of care, or alternatively a combination of from three to eight medications such as, for example, cytarabine, daunorubicin, idarubicin, thioguanine, mitoxantrone, etoposide, and methotrexate. While current chemotherapy can result in complete remissions, the long term disease-free survival rate for leukaemias, in particular AML, is low.

Alternative treatment approaches are directed to developing less toxic and more efficacious therapies. A variety of novel chemotherapeutic agents have been evaluated in AML including topoisomerase I inhibitors such as topotecan and campothecin, platinum containing agents (carboplatin) and new anti-metabolites including gemcitabine, troxcitabine and clofarabine (Smith M, et al., Critical Reviews in Oncology/Hematology. 2004; 50(3): 197-222). All of these agents have activity against leukaemic blasts but their use remains investigational. MDR-1 blockade using cyclosporine A or PSC 833 is not of proven benefit and may either increase toxicity or necessitate dose reduction and hence reduce overall chemotherapy exposure (Larson R A. et al, Leukemia 2003; 17: 488-91).

Because chemotherapy also usually kills normal cells, patients receiving chemotherapy often experience side effects such as, for example, nausea, fatigue, and higher risk of infection.

Therefore, there is a clear and unmet need for effective therapeutics for treatment of haematologic malignancies, including leukaemias, with reduced toxicity.

SUMMARY OF THE INVENTION

In a first aspect, the invention relates to a serotonin receptor (5-HTR) inhibitor selected from the group consisting of a type 1 5-HTR inhibitor and a type 2 5-HTR inhibitor for use in the prevention and/or treatment of a haematological malignancy.

In a second aspect, the invention relates to an in vitro method for the identification of a malignant cell from a haematological malignancy in a sample selected from the group consisting of bone marrow, blood and lymph nodes, said method comprising detecting the expression of type 1 5-HTR and/or type 2 5-HTR in said cell.

In a third aspect, the invention relates to an in vitro method for diagnosing a haematological malignancy in a subject which comprises identifying malignant cells by a method of the invention.

In a fourth aspect, the invention relates to an in vitro method for the isolation of a malignant cell from a haematological malignancy in a sample selected from the group consisting of bone marrow, blood and lymph nodes, said method comprising detecting the expression of type 1 5-HTR and/or type 2 5-HTR in said cell and isolating said cell expressing said 5-HTR.

In a fifth aspect, the invention relates to an in vitro method for determining the prognosis of a subject suffering from a haematological malignancy which comprises:
(a) determining the expression level of type 1 5-HTR and/or type 2 5-HTR in cells of a sample from said subject selected from the group consisting of bone marrow, blood and lymph nodes, and
(b) comparing said level with a reference value
wherein a decrease of the expression level of type 1 5-HTR and/or type 2 5-HTR with respect to the reference value is indicative that the subject shows a good prognosis or wherein an increase of the expression level of type 1 5-HTR and/or type 2 5-HTR with respect to the reference value is indicative that the subject shows a bad prognosis.

In a sixth aspect, the invention relates to an in vitro method for monitoring the effect of a therapy in a subject suffering from a haematological malignancy and being treated with said therapy which comprises:
a) determining the expression level of type 1 5-HTR and/or type 2 5-HTR in cells of a sample from said subject selected from the group consisting of bone marrow, blood and lymph nodes, and
b) comparing said level with the expression level of type 1 5-HTR and/or type 2 5-HTR in cells of a sample from said subject at an earlier point of time wherein a decrease of the expression level of type 1 5-HTR and/or type 2 5-HTR with respect to the level determined in a sample from said subject at an earlier point of time is indicative that the therapy is being effective or wherein an increase of the expression level of type 1 5-HTR and/or type 2 5-HTR with respect to the level determined in a sample from said subject at an earlier point of time is indicative that the therapy is being ineffective.

In a seventh aspect, the invention relates to an in vitro method for designing a customized therapy for a subject diagnosed with a haematological malignancy which comprises
a) determining the levels of the type 1 5-HTR and/or type 2 5-HTR-expressing cells in a sample from said subject selected from the group consisting of bone marrow, blood and lymph nodes, and
b) comparing said levels with a reference value wherein increased levels of type 1 5-HTR and/or type 2 5-HTR-expressing cells with respect to the reference value are indicative that the subject is to be treated with a type 1 5-HTR inhibitor and/or a type 2 5-HTR inhibitor.

Blood cells were identified based on their CD45 expression and SSC profile by cytometry. Nuclear cells were identified by Hoechst positive staining, while death cells were excluded by 7-AAD positive staining. Cell number was calculated by volumetric count. 4 primary donor samples were analyzed in triplicates. Bars represent the cell viability mean of each replicate and error bars indicate the standard deviation. *$p<0.05$.

Figure 9:
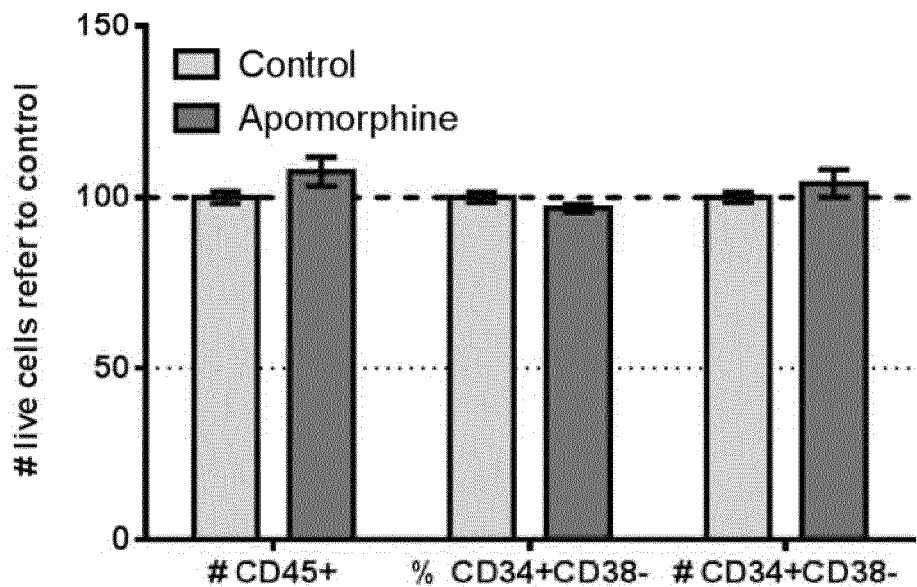

FIG. 9. 5HTR antagonist treatment spared healthy hematopoietic stem/progenitor cells. $2\times10^5$ lineage-depleted ficoll-isolated mononuclear cells from umbilical cord blood samples obtained from healthy donors were treated with Apomorphine at 10 µM in complete IMDM media for 24 h at 37° C. and 5% $CO_2$. Blood cells were identified based on their CD45 expression and SSC profile by cytometry. CD34 and CD38 surface staining were performed to identify each subpopulation. Nuclear cells were identified by Hoechst positive staining, while death cells were excluded by 7-AAD positive staining. Cell number was calculated by volumetric count. 3 primary umbilical cord blood samples were analyzed in triplicates. Bars represent the cell viability mean of each replicate and error bars indicate the standard deviation.

Figure 10:
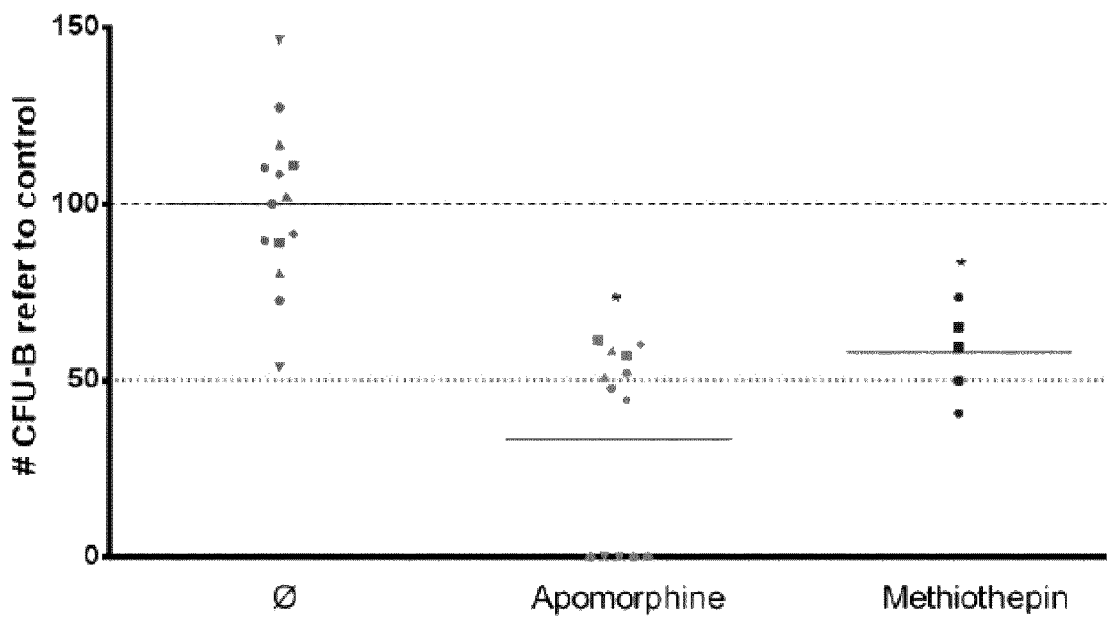

FIG. 10. The clonogenic capacity of primary AML samples is reduced upon 5HTR antagonist treatment. $5\times10^5$ primary patient AML blood cells per mL were treated with Apomorphine or Methiothepin at 10 µM in complete IMDM media for 18 h at 37° C. and 5% $CO_2$. Cells were then cultivated in Methylcellulose supplemented with hematopoietic cytokines for 14 days. The number of CFU-B obtained was measured by microscopy based on morphological criteria. 7 primary AML blood samples were analyzed. Each symbol represents a specific patient sample. Lines represent the median. *$p<0.05$. CFU-B: Blast colony-forming units.

Figure 11:
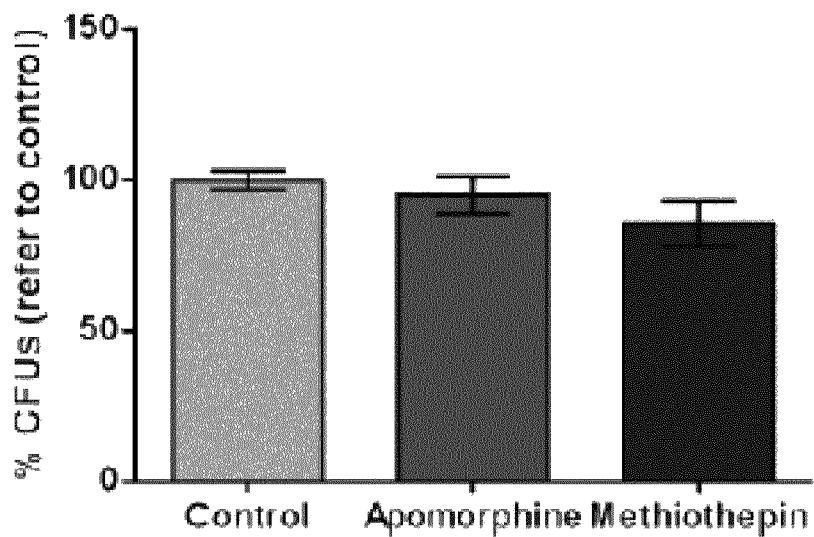
Figure 11:
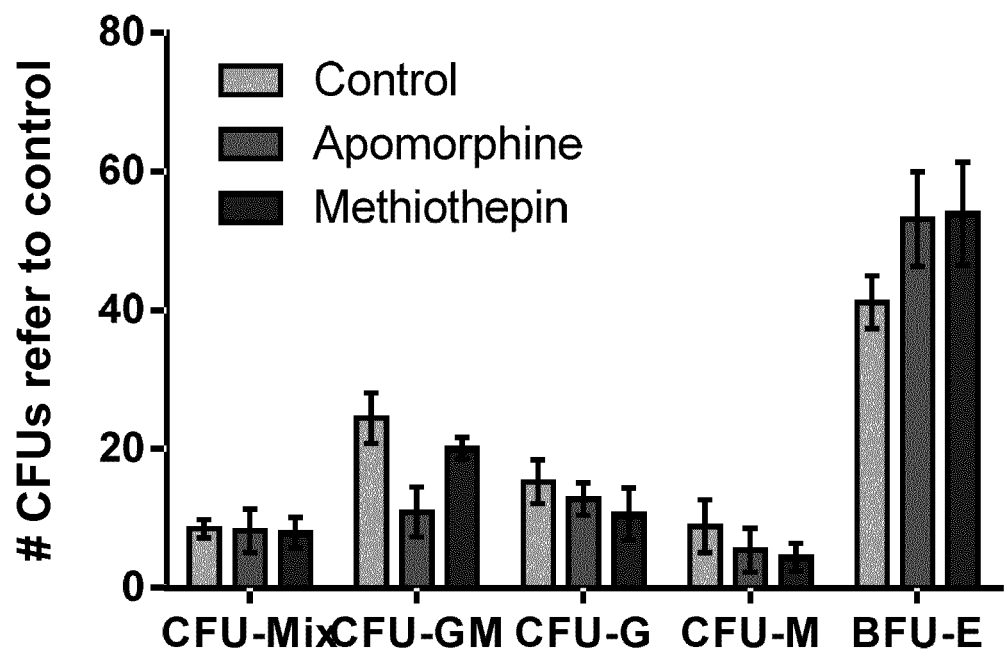

FIG. 11. 5HTR antagonist treatment did not decrease the clonogenic capacity of healthy haematopoietic stem cells. $1\times10^3$ primary lineage-depleted umbilical cord blood cells per mL were treated with Apomorphine or Methiothepin at 10 µM in complete IMDM media for 18 h at 37° C. and 5% $CO_2$. Cells were then cultivated in Methylcellulose supplemented with haematopoietic cytokines for 14 days. The number of colonies obtained was measured by microscopy based on morphological criteria. A. Total number of colonies is represented. CFU: colony-forming units. B. Frequency of each colony subtype is shown (CFU-Mix, Mix lineaged colony; CFU-GM, granulo-monocyte colony; CFU-G, granulocyte colony; CFU-M, monocyte colony; BFU-E erythrocyte blast colony). 4 primary umbilical cord blood samples were analyzed. Bars represent the cell viability mean of each replicate and error bars indicate the standard deviation. *$p<0.05$.

Figure 12:
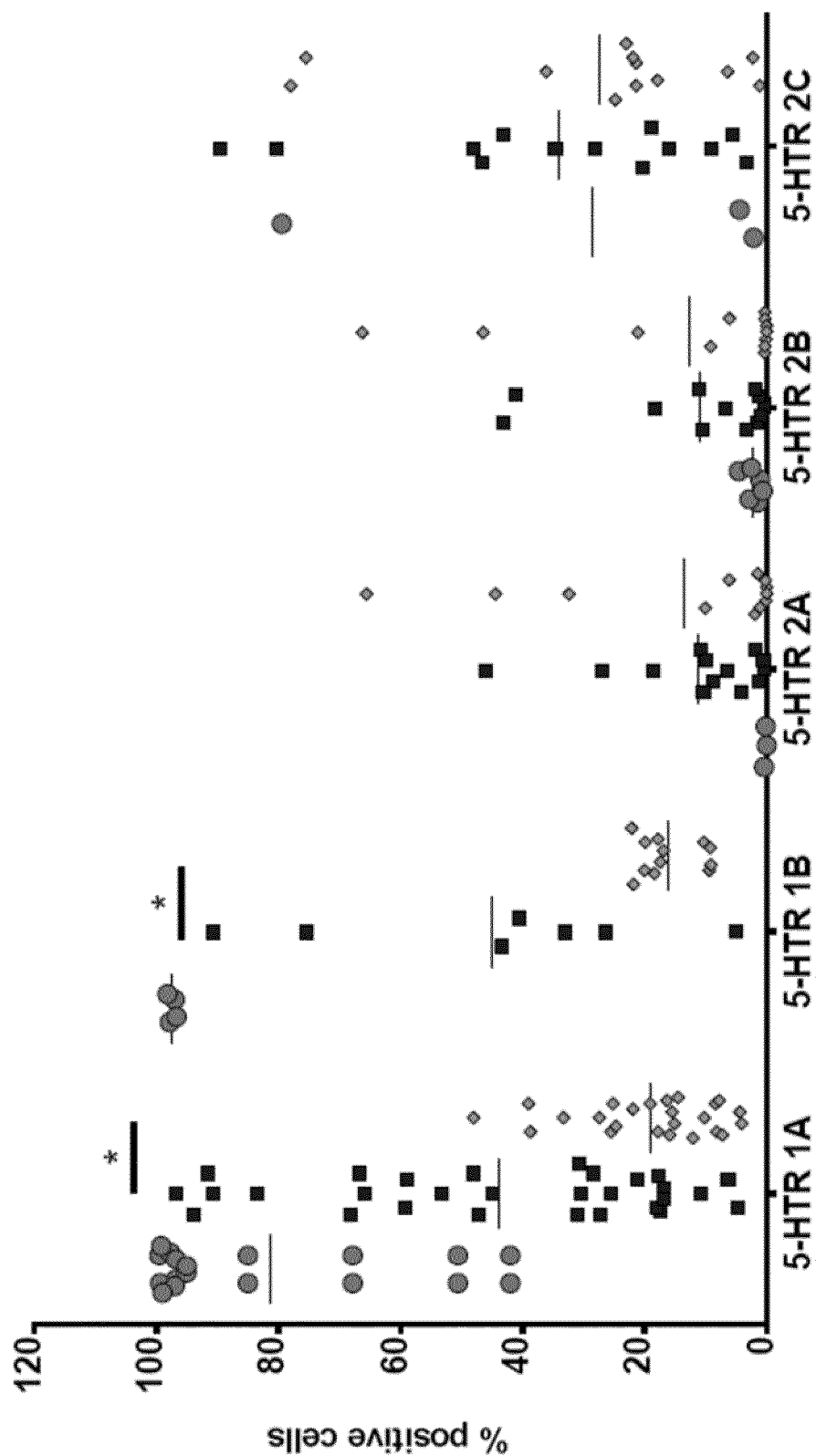

FIG. 12. AML samples differentially express 5HTRs. Primary AML blood samples, healthy peripheral blood samples and AML cell lines (HL-60, KG-1, MonoMac-1 and Kasumi-1) were staining on the surface for 5HTR 1A and HTR1B. Samples were analyzed by flow cytometry and the frequency of positive cells is represented. 18 primary patient AML peripheral blood samples and 16 healthy donor peripheral blood samples are represented. Circles: AML cell lines, Squares: AML, Diamonds: healthy mature blood cells *$p<0.05$; ***$p<0.001$.

Figure 13:
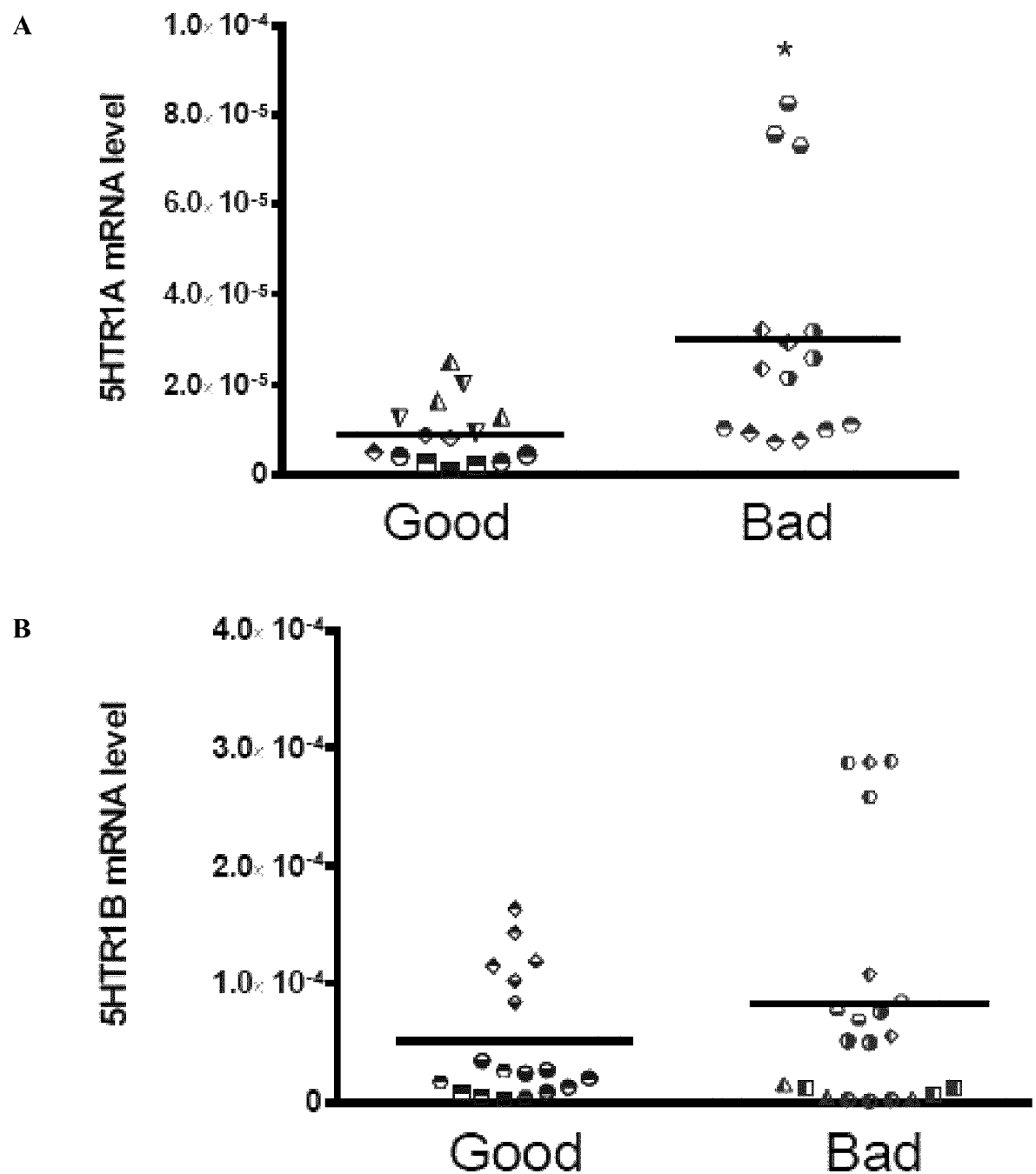

FIG. 13. 5HTR mRNA levels correlates with AML clinical outcome. Total RNA from primary patient AML blood samples was isolated and 5HTR1A (A) and 5HTR1B (B) mRNA levels were measured by semi-quantitative PCR. Expression level was normalized against GAPDH and calculated following the $2^{\Delta Ct}$ method. 6 AML samples corresponding to the good prognosis group and 8 AML samples corresponding to the bad prognosis group are represented in triplicates. *$p<0.05$.

Figure 14:
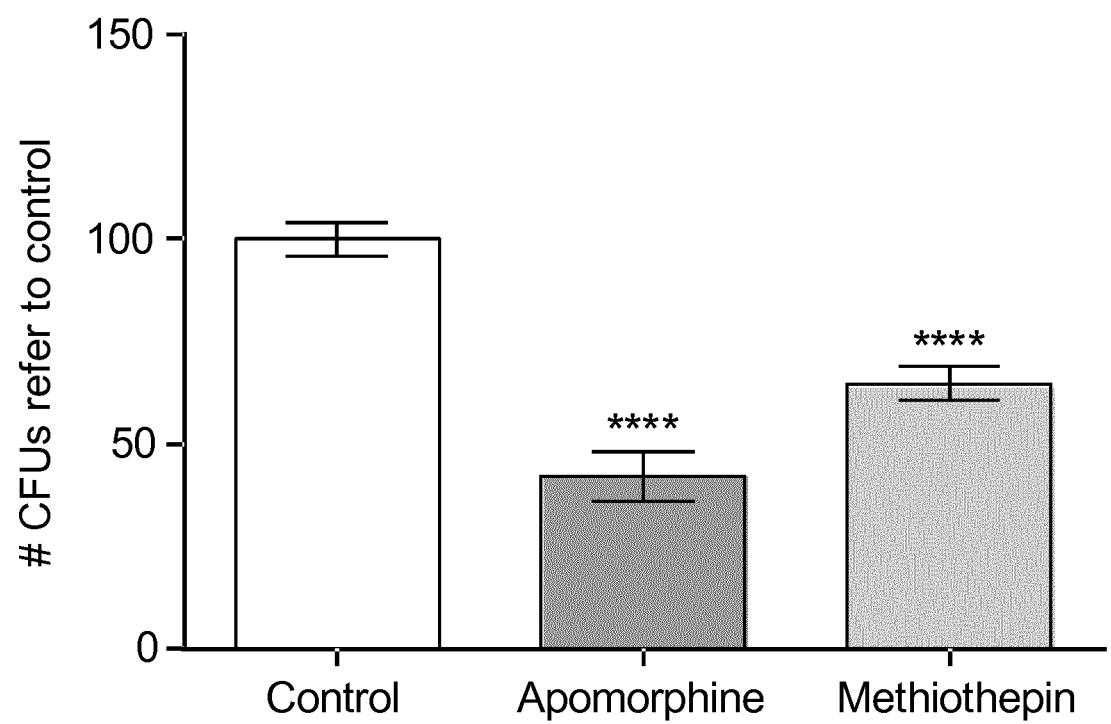

FIG. 14. Treatment with 5HTR antagonists produce a reduction in secondary CFUs. $10^6$ primary AML patient cells per mL from primary CFUs pretreated with 10 µM apomorphine, 10 µM methiothepin or vehicle control were replated in methylcellulose supplemented with hematopoietic cytokines for 14 days. The number of CFU-Bs obtained was measured by microscopy based on morphological criteria. Three primary AML samples were tested. *$p<0.05$, *$p<0.005$, **$p<0.001$.

Figure 15:
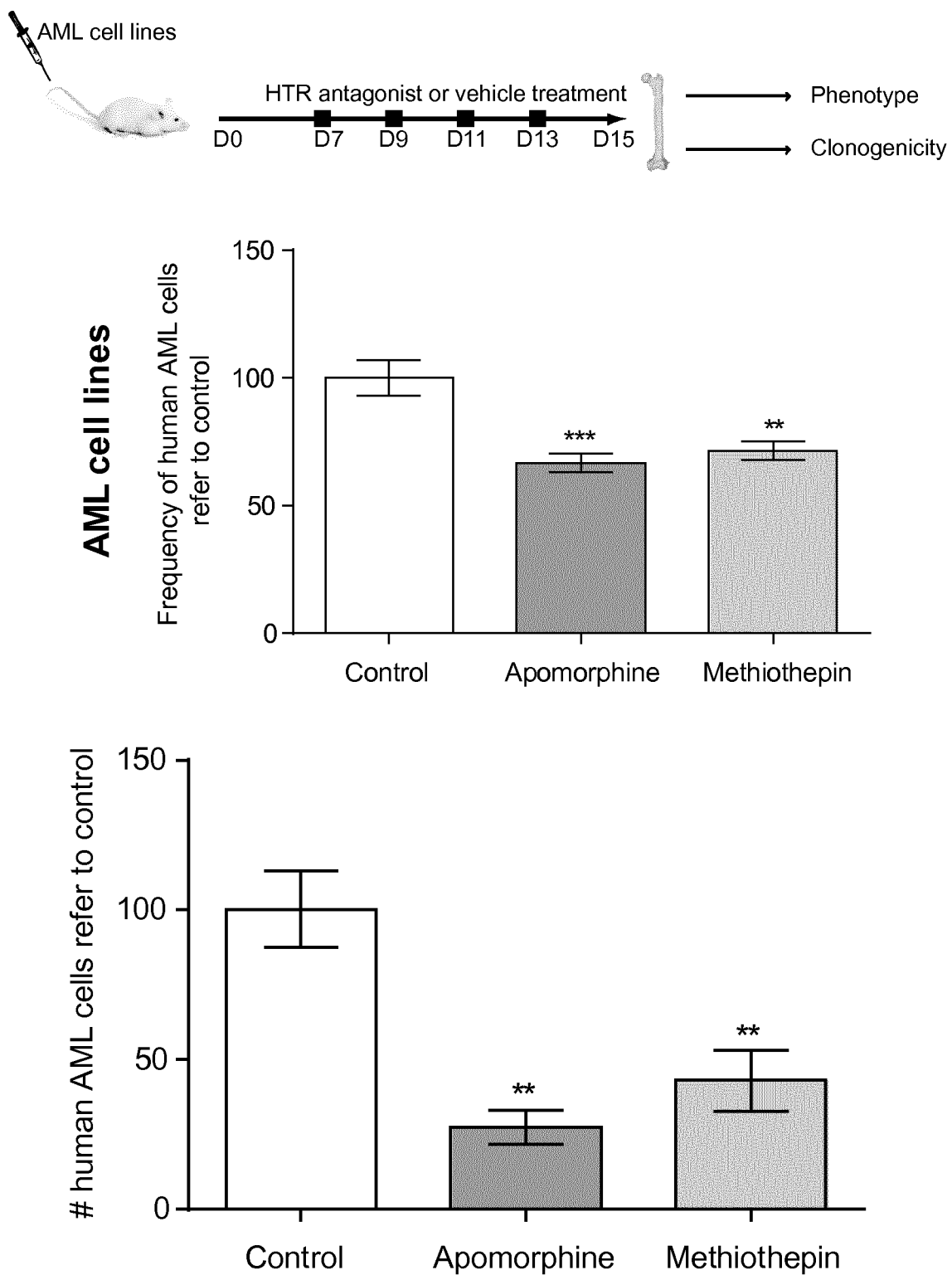

FIG. 15. Treatment with 5HTR1 antagonists reduce AML burden in an in vivo xenotransplantation mouse model. 6-8 week-old NOD.Cg-Prkdc$^{scid}$ Il2rg$^{tm1Wjl}$/SzJ (NSG) mice were myeloablated with busulfan (30 mg/kg IP) at day 0. At day 1, $10^6$ MonoMac-1 cells were injected IV. From day 7 to day 14, mice were treated IP every other day with apomorphine (5 mg/kg) or methiothepin (0.1 mg/kg), while control mice were treated with saline vehicle (0.9% NaCl). At day 15, mice were sacrificed and their bones (iliac crests, femurs and tibias) were harvested and analyzed for the presence of human cells. Bone marrow samples were measured by flow cytometry. Frequency of human CD45 positive cells (upper panel) and total human CD45 positive cells (lower panel) in BM refer to control. Bars represent the mean value. Error bars represent SEM. $p<0.01$; *$p<0.001$.

Figure 16:
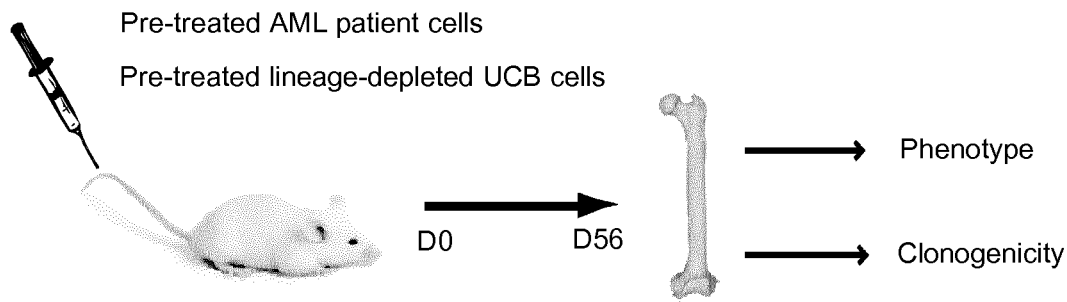
Figure 16:
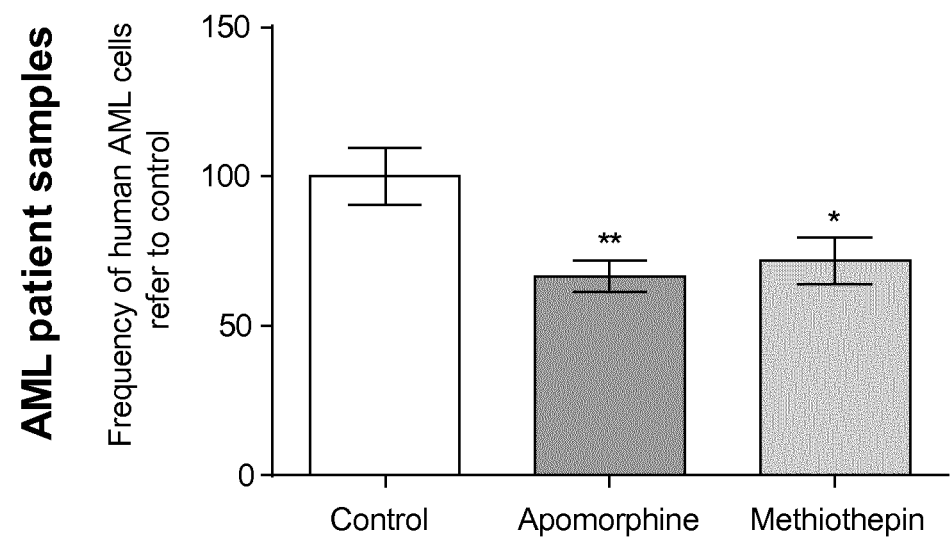
Figure 16:
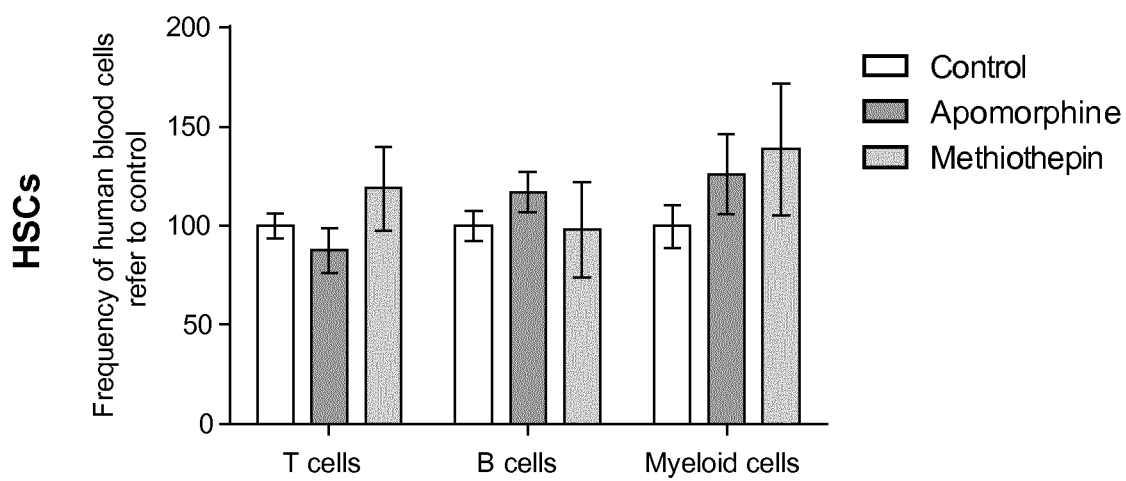

FIG. 16. 5HTR antagonist treatment reduces the leukemia regeneration capacity of primary AML cells, whilst sparing healthy hematopoietic stem/progenitor cells. $1\text{-}10\times10^6$ primary AML patient cells or $10\text{-}14\times10^4$ lineage-depleted CB cells were ex vivo treated (10 µM apomorphine, 10 µM methiothepin or vehicle control) for 18 h in IMDM supplemented with 5% heat-inactivated fetal bovine serum and hematopoietic cytokines. Cells were injected IV in previously busulfan (30 mg/kg)-conditioned NSG mice and left 8 weeks untreated. Mice were sacrificed and their bones (iliac crests, femurs and tibias) were harvested and analyzed for the presence of human leukemia (upper panel) or healthy blood (lower panel) cells by flow cytometry. Four AML patient samples and three umbilical cord blood (UCB) samples were tested. *$p<0.05$; **$p<0.01$.

Figure 17:
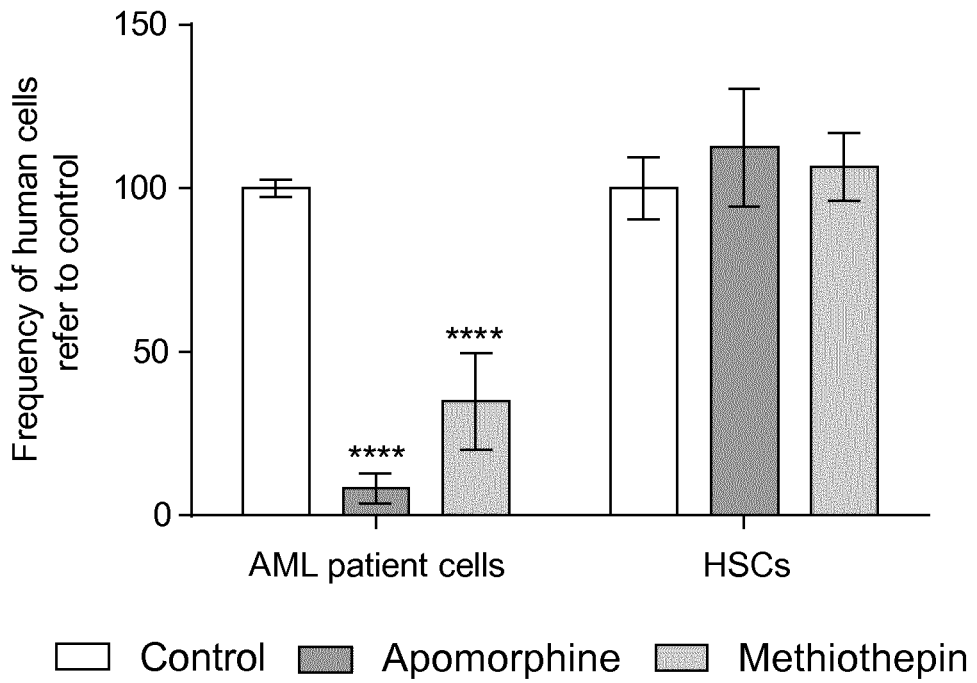
Figure 17:
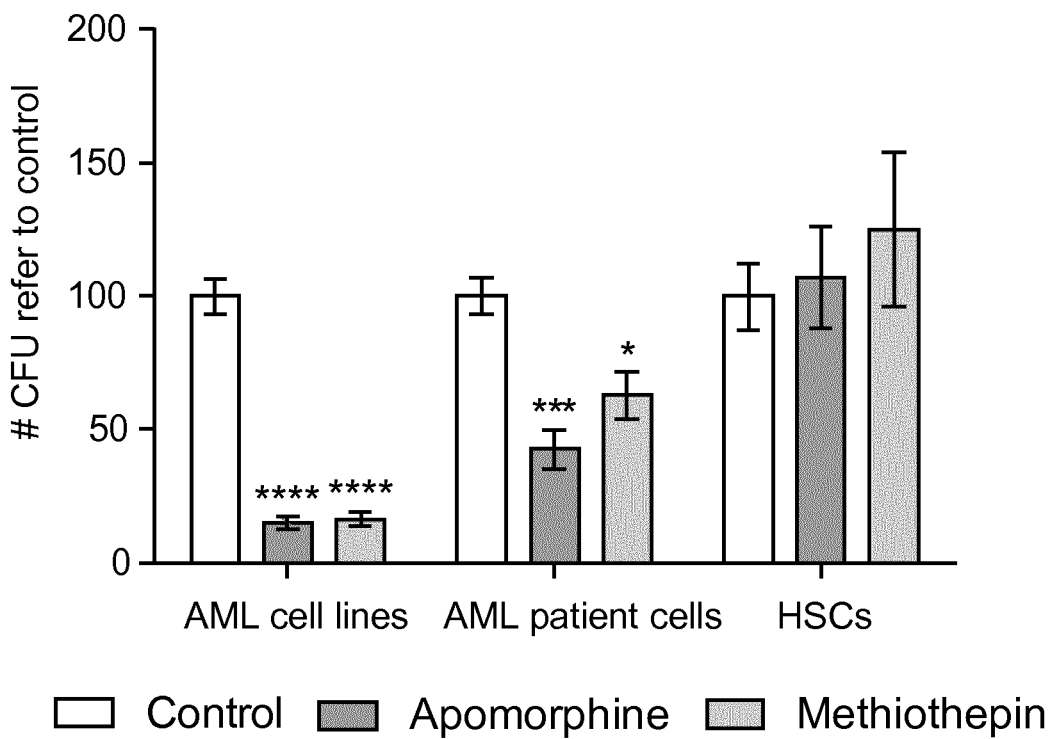

FIG. 17. Treatments with 5HTR antagonists reduce the leukemia regeneration capacity of primary AML samples in secondary recipient, without affecting normal hematopoiesis. Upper panel. $3\text{-}10\times10^5$ engrafted bone marrow cells from primary transplanted mice were injected intravenously into secondary recipients (conditioned NSG mice) and left untreated for 8 weeks. Bone marrow cells were analyzed as in FIG. 16. Frequency of human CD45 positive cells referred to control is represented. Lower panel. $50\times10^3$ engrafted human cells were screened for CFUs. The normalized number of CFUs obtained is represented. *$p<0.05$; *$p<0.005$; **$p<0.0001$.

DETAILED DESCRIPTION OF THE INVENTION

The inventors of the present invention have found that haematological malignant cells, particularly AML cells, express serotonin receptors (5HTR) and that inhibition of type 1 and/or type 2 5HTR has cytotoxic effect on AML cells, as shown in Examples 1 and 2, reduces the clonogenic capacity of AML blasts while sparing healthy hematopoietic stem cells (Example 5), and that type 1 and/or type 2 5-HTR inhibitors have no effect neither on healthy blood cells nor on healthy haematopoietic stem/progenitor cells (Example 4). Additionally, they have observed that the detection of the expression of type 1 5-HTR and/or type 2 5-HTR can be used for the identification of a malignant cell from a haematological malignancy (Example 6), and that a decrease in the expression of type 1 5-HTR and/or type 2 5-HTR in a sample from a patient suffering a haematological malignancy correlates with good prognosis (Example 7).

Definitions

"Serotonin receptors", also known as 5-hydroxytryptamine receptors or 5-HT receptors or 5-HTR, as used herein, are a group of G protein-coupled receptors (GPCRs) and ligand-gated ion channels (LGICs) found in the central and peripheral nervous systems.

The term "type 1 5-HT receptor" or "type 1 5-HTR" or "5-HT1 receptor" or "5-HTR1", as used herein, relates to a subfamily of 5-HT receptors that bind the endogenous neurotransmitter serotonin (5-hydroxytryptamine, 5-HT). The 5-HT1 receptor subfamily consists of five G protein-coupled receptors (GPCRs) that are coupled to Gi/Go and the term includes 5-HTR1A, 5-HTR1B, 5-HTR1D, 5-HTR1E, and 5-HTR1F. These receptors mediate inhibitory neurotransmission by decreasing cellular levels of cAMP. The complete protein sequence for human type 1A 5-HT receptor has the UniProt accession number P08908 (Apr. 16, 2014). The complete protein sequence for human type 1B 5-HT receptor has the UniProt accession number P28222 (Apr. 16, 2014). The complete protein sequence for human type 1D 5-HT receptor has the UniProt accession number P28221 (Apr. 16, 2014). The complete protein sequence for human type 1E 5-HT receptor has the UniProt accession number P28566 (May 14, 2014). The complete protein sequence for human type 1F 5-HT receptor has the UniProt accession number P30939 (Apr. 16, 2014).

The term "type 2 5-HT receptor" or "type 2 5-HTR" or "5-HT2 receptor" or "5-HTR2", as used herein, refers to a subfamily of 5-HT receptors that bind the endogenous neurotransmitter serotonin (5-hydroxytryptamine, 5-HT). The 5-HT2 receptor subfamily consists of three G protein-coupled receptors (GPCRs) which are coupled to Gq/G11 and the term includes 5-HTR2A, 5-HTR2B, and 5-HTR2C. These receptors mediate excitatory neurotransmission by increasing cellular levels of IP3 and DAG. The complete protein sequence for human type 2A 5-HT receptor has the UniProt accession number P28223 (May 14, 2014), for human type 2B 5-HT receptor has the UniProt accession number P41595 (May 14, 2014) and for human type 2C 5-HT receptor has the UniProt accession number P28335 (May 14, 2014).

The term "inhibitor", as used herein, refers to a compound inhibiting the activity of the 5-HT receptor. The term inhibitor includes, without limitation, antagonists of the 5-HT receptor, antibodies against the 5-HT receptor, compounds which prevent expression of the 5-HT receptor and compounds which lead to reduced mRNA or protein levels of the 5-HT receptor. In a preferred embodiment the inhibitor is an antagonist. In the context of the present invention, the term "antagonist" refers to a compound that binds to the 5-HT receptor and lacks any substantial ability to activate the receptor itself. An antagonist can thereby prevent or reduce the functional activation or occupation of the receptor by an agonist or the natural ligand when the agonist is present. The term "antagonist of the 5-HT receptor", as used herein, is intended to encompass both neutral antagonists and inverse agonists. A "neutral antagonist" is a compound that blocks the action of the agonist but has no effect on intrinsic or spontaneous receptor activity. An "inverse agonist" is able to both block the action of the agonist at the receptor and attenuate the constitutive activity of the receptor. The term "antagonist" also includes competitive antagonists, which are drugs that bind to the same site as the natural ligand; noncompetitive antagonists which bind to a different site on the receptor than the natural ligand; reversible antagonists which bind and unbind the receptor at rates determined by receptor-ligand kinetics; and irreversible antagonists which bind permanently to the receptor either by forming a covalent bond to the active site or just by binding so tightly that the rate of dissociation is effectively zero.

The term "type 1 5-HTR inhibitor", as used herein, refers to any compound capable of inhibiting the activity of the 5-HTR1 (for example by binding to the 5-HTR1 and lacking any substantial ability to activate the receptor itself; or by preventing or reducing the expression of 5-HTR1 mRNA or 5-HTR1 protein). This term includes selective inhibitors for the 5-HTR1 or for any of the 5-HTR1 subtypes (5-HTR1A, 5-HTR1B, 5-HTR1D, 5-HTR1E, and 5-HTR1F) and non-selective inhibitors that are also capable of acting as inhibitors on 5-HT receptors from other subfamilies.

The term "type 2 5-HTR inhibitor", as used herein, refers to any compound capable of inhibiting the activity of the 5-HTR2 (for example by binding to the 5-HTR2 and lacking any substantial ability to activate the receptor itself; or by preventing or reducing the expression of 5-HTR2 mRNA or 5-HTR2 protein). This term includes selective inhibitors for the 5-HTR2 or for any of the 5-HTR2 subtypes (5-HTR2A, 5-HTR2B and 5-HTR2C) and non-selective inhibitors that are also capable of acting as inhibitors on 5-HT receptors from other subfamilies.

"Apomorphine", as used herein, refers to (6aR)-6-methyl-5,6,6a,7-tetrahydro-4H-dibenzo[de,g]quinoline-10,11-diol, CAS number 314-19-2. Apomorphine is a type 1 and type 2 5-HTR antagonist (Millan M. J. et al. 2002. J Pharmacol Exp Ther, 303(2):791-804). In an embodiment, the inhibitor is apomorphine.

"Methiothepin" or metitepine, refers to 1-methyl-4-(8-methylsulfanyl-5,6-dihydrobenzo[b][1]benzothiepin-6-yl)piperazine, CAS number 74611-28-2. Methiothepin is a type 1 and type 2 5-HTR antagonist (Kawano H. et al. 2001. Blood, 97(6):1697-1702), particularly an inverse agonist. In an embodiment, the inhibitor is methiothepin.

"Amperozide", as used herein, refers to 4-[4,4-bis(4-fluorophenyl)butyl]-N-ethylpiperazine-1-carboxamide, CAS number 75558-90-6. Amperozide is a type 2 5-HTR antagonist (Svartengren J. and Simonsson P. Pharmacol Toxicol, 1990; 66 suppl 1:8-11). In an embodiment, the inhibitor is amperozide.

The term "haematological malignancy" refers to types of cancer that affect blood, bone marrow, and lymph nodes. Haematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukaemias, and myelomas are from the lymphoid line, while acute and chronic myelogenous leukaemia, myelodysplastic syndromes and myeloproliferative diseases are myeloid in origin. Non limitative, illustrative examples of haematological malignancies are Acute lymphoblastic leukaemia (ALL), Acute myelogenous leukaemia (AML), Chronic lymphocytic leukaemia (CLL), Chronic myelogenous leukaemia (CML), Acute monocytic leukaemia (AMoL), Hodgkin's lymphomas, non-Hodgkin's lymphomas and myelomas.

"Leukaemia", as used herein, refers to a type of cancer of the blood or bone marrow characterized by an abnormal increase of immature white blood cells called "blasts". Leukaemia is a broad term covering a spectrum of diseases. In turn, it is part of the even broader group of diseases affecting the blood, bone marrow, and lymphoid system, which are all known as haematological neoplasms. There are four major kinds of leukaemia: Acute lymphoblastic leukaemia, or ALL; Acute myeloid leukaemia, or AML; Chronic lymphocytic leukaemia, or CLL; Chronic myelogenous leukaemia, or CML.

"Acute lymphoblastic leukaemia (ALL) or acute lymphoid leukaemia" is an acute form of leukaemia, or cancer of the white blood cells, characterized by the overproduction of cancerous, immature white blood cells—known as lymphoblasts.

"Acute Myeloid Leukaemia (AML) or acute myelogenous leukaemia or acute nonlymphocytic leukaemia (ANLL)" is a cancer of the myeloid line of blood cells, characterized by the rapid growth of abnormal white blood cells (mieloblasts) that accumulate in the bone marrow and interfere with the production of normal blood cells. The symptoms of AML are caused by replacement of normal bone marrow with leukaemic cells, which causes a drop in red blood cells, platelets and normal white blood cells. The combination of a myeloperoxidase or Sudan black stain and a nonspecific esterase stain on blood and blood marrow smears are helpful in distinguishing AML from ALL.

"Chronic lymphocytic leukaemia (CLL) or B-cell chronic lymphocytic leukaemia (B-CLL)" is a type of cancer that causes the body to produce large numbers of white blood cells (B cell lymphocytes).

"Chronic myelogenous leukaemia (CML)" also known as "chronic granulocytic leukaemia (CGL)" is a type of cancer that causes the body to produce large numbers of white blood cells (myelocytes). In CML a proliferation of mature granulocytes (neutrophils, eosinophils and basophils) and their precursors is found. It is associated with a characteristic chromosomal translocation called the Philadelphia chromosome.

"Sample", as used herein, refers to a sample selected from the group consisting of bone marrow, blood and lymph nodes.

"Peripheral blood", as used herein, refers to a sample comprising the cellular components of blood, consisting of red blood cells, white blood cells, and platelets, which are found within the circulating pool of blood and not sequestered within the lymphatic system, spleen, liver, or bone marrow.

"Malignant cell", as used herein, is a "tumour cell" or "cancer cell" and refers to cells that grow and divide at an unregulated, quickened pace.

The term "subject" or "individual" or "animal" or "patient" includes any subject, particularly a mammalian subject, for whom therapy is desired. Mammalian subjects include humans, domestic animals, farm animals, and zoo or pet animals such as dogs, cats, guinea pigs, rabbits, rats, mice, horses, cattle, cows, and so on.

"Immunocytochemistry" refers to a technique used to localize the presence of a specific protein or antigen in cells by use of a specific primary antibody that binds to it wherein the extracellular matrix and other stromal components are removed, leaving only whole cells to stain.

The term "decrease of the expression level" refers to the level of expression of type 1 5-HTR and/or type 2 5-HTR which is lower than a reference value. The expression level is considered to be lower than a reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more lower than its reference value.

The term "increase of the expression level" is referred to the level of expression of type 1 5-HTR and/or type 2 5-HTR which is higher than a reference value. The levels of expression are considered to be higher than its reference value when they are at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more higher than its reference value.

The term "reference value", as used herein, relates to a predetermined criteria used as a reference for evaluating the values or data obtained from the samples collected from a subject. The reference value or reference level can be an absolute value; a relative value; a value that has an upper or a lower limit; a range of values; an average value; a median value; a mean value; or a value as compared to a particular control or baseline value. A reference value can be based on an individual sample value, such as for example, a value obtained from a sample from the subject being tested, but at an earlier point in time. The reference value can be based on a large number of samples, such as from population of subjects of the chronological age matched group, or based on a pool of samples including or excluding the sample to be tested.

"Good prognosis", as used herein, means an outcome which would be regarded positive for the patient and depends on the prognosis type; for example, a good prognosis of 1 year survival (1YS) would mean that the patient will survive for at least 1 year. In a preferred embodiment, good prognosis relates to a probability over 40% of 5 year survival after diagnosis of the disease.

"Bad prognosis", as used herein, means an outcome which would be regarded negative for the patient and depends on the prognosis type; for example, a bad prognosis of 1 year survival would mean that the patient will not survive for at least 1 year. In a preferred embodiment, bad prognosis relates to a probability under 40% of 5 year survival after diagnosis of the disease.

"Earlier point of time", as used herein, refers to any moment before the therapy is administered to a subject suffering from a haematological malignancy.

"Effective therapy", as used herein, refers to a therapy that leads to reduced levels of type 1 5-HTR and/or type 2 5-TR in a sample of the patient suffering from a haematological malignancy and being treated with said therapy.

"Ineffective therapy", as used herein, refers to a therapy that does not help to reduce the level of type 1 5-HTR and/or type 2 5-HTR in a sample of the patient suffering from a haematological malignancy and being treated with said therapy.

1—Medical Uses

The authors of the present invention have found that type 1 5-HTR and type 2 5-HTR inhibitors are therapeutically effective in the treatment of a haematological malignancy, preferably AML, and that said inhibitors have no effect neither on healthy blood cells nor on healthy haematopoietic stem cells, thus avoiding toxicity over normal cells produced by classical chemotherapeutic treatments.

In a first aspect, the invention relates to a serotonin receptor (5-HTR) inhibitor selected from the group consisting of a type 1 5-HTR inhibitor and a type 2 5-HTR inhibitor for use in the prevention and/or treatment of a haematological malignancy.

Alternatively, the invention relates to the use of a serotonin receptor (5-HTR) inhibitor selected from the group consisting of a type 1 5-HTR inhibitor and a type 2 5-HTR inhibitor for the preparation of a medicament for the prevention and/or treatment of a haematological malignancy.

Alternatively, the invention relates to a method for preventing and/or treating a haematological malignancy comprising administering a serotonin receptor (5-HTR) inhibitor selected from the group consisting of a type 1 5-HTR inhibitor and a type 2 5-HTR inhibitor to a subject in need thereof.

The term "prevention", "preventing" or "prevent", as used herein, relates to the administration of an inhibitor according to the invention or of a medicament comprising said inhibitor to a subject who has not been diagnosed as possibly having a haematological malignancy at the time of administration, but who would normally be expected to develop said disease or be at increased risk for said disease. The prevention intends to avoid the appearance of said disease. The prevention may be complete (e.g. the total absence of a disease). The prevention may also be partial, such that for example the occurrence of a disease in a subject is less than that which would have occurred without the administration of the inhibitor of the present invention. Prevention also refers to reduced susceptibility to a clinical condition.

The term "treatment", as used herein, relates to the administration of an inhibitor according to the invention or of a medicament comprising said inhibitor to a subject suffering from a haematological malignancy including the administration in an initial or early stage of a disease, wherein the object is to prevent or slow down (lessen) an undesired physiological change or disorder. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Treatment also means prolonging survival as compared to expected survival if not receiving the treatment.

In a preferred embodiment the type 1 5-HTR inhibitor is selected from the group consisting of type 1A, type 1B, type 1D, type 1E and type 1F 5-HTR inhibitor; preferably is type 1A 5-HTR inhibitor.

In another preferred embodiment the type 2 5-HTR inhibitor is selected from the group consisting of type 2A, type 2B and type 2C 5-HTR inhibitor; preferably is selected from type 2B and type 2C 5-HTR inhibitor; more preferably is type 2C 5-HTR inhibitor.

The person skilled in the art knows how to determine the affinity of a particular molecule for a type 1 5-HTR and/or a type 2 5-HTR and also to determine if this particular molecule is an inhibitor of said receptor. For example, the 5-HTR affinity of a molecule can be determined using the methodology described by Millan et al. (Millan et al. J Pharmacol Exp Ther. 2002; 303(2):791-804) (radioligand binding assay) An assay to assess if a compound is a type 1 5-HTR inhibitor is the determination of the Gi activation status and measuring the cAMP production and activation of adenylyl cyclase (Nichols D. E. and Nichols C. E. Chem Rev, 2008; 108(5):1614-41). An assay to assess if a compound is a type 2 5-HTR inhibitor is the measurement of membrane phosphoinositides hydrolysis and activation of PKC (Nichols D. E. and Nichols C. E. Chem Rev, 2008; 108(5):1614-41). Assays that can be performed by the person skilled in the art to distinguish if the type 1 5-HTR inhibitor is type 1A, type 1B, type 1D, type 1E or type 1F 5-HTR inhibitor are competitive activation assays with subtype-specific agonists. Assays that can be performed by the person skilled in the art to distinguish if the type 2 5-HTR inhibitor is type 2A, type 2B and type 2C 5-HTR inhibitor are competitive activation assays using subtype-specific agonists.

In an embodiment, the 5-HTR inhibitor is a non-selective inhibitor that may act as inhibitor for different types of 5-HTR. In another embodiment, the 5-HTR inhibitor is selective for a type 1 5-HTR and/or a type 2 5-HTR.

The type 1 or type 2 5-HTR inhibitors can be, among others, proteins, peptides, interference RNA, antisense oligonucleotides or small organic molecules.

In a preferred embodiment, the type 1 5-HTR inhibitor and/or type 2 5-HTR inhibitor is selected from the compounds of Table 1 or pharmaceutically acceptable salts thereof.

TABLE 1

INHIBITORS OF TYPE 1 AND/OR TYPE 2 5-HTR FOR USE ACCORDING TO THE INVENTION

| | |
|---|---|
| I | 5-HT1A antagonists such as |
| | Methiothepin |
| | Apomorphine |
| | BMY 7378 |
| | Cyanopindolol |
| | Iodocyanopindolol |
| | Lecozotan |
| | Methysergide |
| | NAN-190 |
| | Nebivolol |
| | Nefazodone |
| | WAY-100,135 |
| | WAY-100,635 |
| | Mefway |
| II | 5-HT1B antagonists such as |
| | Methiothepin |
| | Alprenolol |
| | AR-A000002 |
| | Asenapine |
| | Cyanopindolol |
| | GR-127,935 |
| | Iodocyanopindolol |
| | Isamoltane |
| | Metergoline |
| | Oxprenolol |
| | Pindolol |
| | Propranolol |
| | SB-216,641 |
| | Yohimbine |
| | GR-55562 |
| | SB-224289 |
| | SB-236057 |
| III | 5-HT1D antagonists such as |
| | BRL-15572 |
| | GR-127,935 |
| | Ketanserin |
| | Metergoline |
| | Methiothepin |
| | Rauwolscine |
| | Ritanserin |
| | Vortioxetine |
| | Ziprasidone |
| | SB-714786 |
| IV | 5-HT2A antagonists such as |
| | Apomorphine |
| | Atypical antipsychotics, such as Clozapine, Olanzapin, |

| | INHIBITORS OF TYPE 1 AND/OR TYPE 2 5-HTR FOR USE ACCORDING TO THE INVENTION |
|---|---|
| | Quetiapine, Risperidone, Ziprasidone<br>Aripiprazole<br>Asenapine<br>Amitriptyline<br>Clomipramine<br>Cyproheptadine<br>Eplivanserin<br>Etoperidone<br>Haloperidol<br>Hydroxyzine<br>Iloperidone<br>Ketanserin<br>Methysergide<br>Mianserin<br>Mirtazapine<br>Nefazodone<br>Pimavanserin<br>Pizotifen<br>Ritanserin<br>Trazodone<br>Yohimbine<br>MDL-100907 |
| V | 5-HT2B antagonists such as<br>Apomorphine<br>Agomelatine<br>Asenapine<br>BZP<br>Ketanserin<br>Methysergide<br>Ritanserin<br>RS-127,445<br>Tegaserod<br>Yohimbine<br>SB-200646<br>SB-204741 |
| VI | 5-HT2C antagonists such as<br>Apomorphine<br>Agomelatine<br>Amitriptyline<br>Asenapine<br>Clomipramine<br>Clozapine<br>Cyproheptadine<br>Dimebolin<br>Eltoprazine<br>Etoperidone<br>Fluoxetine<br>Haloperidol<br>Iloperidone<br>Ketanserin<br>Lisuride<br>Methysergide<br>Mianserin<br>Mirtazapine<br>Nefazodone<br>Olanzapine<br>Paroxetine<br>Quetiapine<br>Risperidone<br>Ritanserin<br>Tramadol<br>Trazodone<br>Ziprasidone<br>SB-242084<br>RS-102221 |
| VII | Other compounds, such as:<br>(S)-UH-301 ((S)-5-fluoro-8-hydroxy-2-dipropylaminotetralin) (Moreau et al., Brain Res. Bull.29, 901-04 (1992))<br>Alprenolol (1-(1-methylethyl)amino-3-[2-(2-propenyl)-phenoxy]-2-propanol) (Brandstrom et al., U.S. Pat. No. 3,466,325)<br>Spiperone (8-[4-(4-fluorophenyl)-4-oxobutyl]-1-phenyl-1,3,8-triazaspiro[4,5]decan-4-one) (U.S. Pat. Nos. 3,155,669 and 3,155,670)<br>Tertatolol (8-(3-t-butylamino-2-hydroxypropyloxy)-thiochroman) (U.S. Pat. No. 3,960,891)<br>Propranolol (1-isopropylamino-3-(1-naphthalenyloxy)-2-propanol) (Crowther et al., U.S. Pat. No. 3,337,628)<br>Penbutolol (1-(t-butylamino)-2-hydroxy-3-(2-cyclopentyl-phenoxy)propane) (Ruschig et al., U.S. Pat. No. 3,551,493)<br>Pindolol (4-(2-hydroxy-3-isopropylaminopropoxy)-indole), (U.S. Pat. No. 3,471,515)<br>The compounds of formula I disclosed in EP 0687472 A2 |
| VIII | Inhibitory antibodies of type 1 and/or type 2 5-HTR |
| IX | An interference RNA specific for the type 1 and/or type 2 5-HTR sequences |
| X | An antisense oligonucleotide specific for the type 1 and/or type 2 5-HTR sequences |
| XI | A ribozyme or DNA enzyme specific for the type 1 and/or type 2 5-HTR sequences |

In a preferred embodiment, the inhibitor is an antagonist, and more preferred and antagonist selected from the group consisting of apomorphine, methiothepin, amperozide and a pharmaceutically acceptable salt thereof. The term "antagonist" has been defined previously. The activity of type 1 5-HTR can be determined by detecting decreasing levels of cAMP (Williams C. Nat Rev Drug Discovery, 2004; 3(2): 125-35) and increasing levels of phosphor-Aid (Suni M A. and Maino V C. Methods Mol Biol 2011; 717:155-69); and the activity of type 2 5-HTR can be determined by detecting increasing levels of IP3 and DAG (Thomsen W., Frazer J. et al. Curr Opin Biotechnol, 2005; 16(6):655-65) and also increasing levels of phosphor-ERK1/2 (Suni M A. and Maino V C. Methods Mol Biol 2011; 717:155-69).

The term "pharmaceutically acceptable salt thereof", as used herein, refers to derivatives of the compounds of Table 1 wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethane-disulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluenesulfonic.

The pharmaceutically acceptable salts of the compounds of Table 1 can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in Remington's Pharmaceutical Sciences, 18$^{th}$ ed., Mack Publishing Company, Easton, Pa., 1990, p. 1445.

In an embodiment, the inhibitor is an inhibitory antibody. The term "inhibitory antibody" is understood to mean, according to the present invention, an antibody that is capable of binding to type 1 5-HTR or type 2 5-HTR provoking the inhibition of the activation of said receptors by its natural ligand. Antibodies may be prepared using any method known by a person skilled in the art. Thus, polyclonal antibodies are prepared by immunization of an animal with the protein aimed to be inhibited. Monoclonal antibodies may be prepared using the method described by Kohler, Milstein et al (Nature, 1975, 256: 495). Once antibodies capable of binding to type 1 5-HTR or type 2 5-HTR are identified, those antibodies capable of inhibiting type 1 5-HTR or type 2 5-HTR activity using the abovementioned assays for determination of type 1 5-HTR or type 2 5-HTR activity will be selected. Suitable antibodies in the present invention include intact antibodies which comprise an antigen-binding variable region and a constant region, fragments "Fab", "F(ab')2", "Fab'", Fv, scFv, diabodies and bispecific antibodies.

In another embodiment, the inhibitor is an interference RNA. As used herein, the term "interference RNA" or "iRNA" refers to RNA molecules capable of silencing the expression of type 1 5-HTR or type 2 5-HTR gene or of any gene needed for type 1 5-HTR or type 2 5-HTR function. To that end, iRNA are typically double-stranded oligonucleotides having at least 30 base pairs in length, and they more preferably comprise about 25, 24, 23, 22, 21, 20, 19, 18 or 17 ribonucleic acid base pairs. Several different types of molecules have been used effectively in iRNA technology including small interfering RNA (siRNA) sometimes known as short interference RNA or silencer RNA, micro RNA (miRNA) which normally differ from siRNA because they are processed from single-stranded RNA precursors and they are shown to be only partially complementary to the target mRNA and short hairpin RNA (shRNA).

Small interfering RNA (siRNA) agents are capable of inhibiting target gene expression by interfering RNA. siRNAs may be chemically synthesized, or may be obtained by in vitro transcription, o may be synthesized in vivo in target cell. Typically, siRNAs consist of a double-stranded RNA from 15 to 40 nucleotides in length and may contain a protuberant region 3' and/or 5' from 1 to 6 nucleotides in length. Length of protuberant region is independent from total length of siRNA molecule. siRNAs act by post-transcriptional degradation or silencing of target messenger.

siRNA may be denominated shRNA (short hairpin RNA) characterized in that the antiparallel strands that form siRNA are connected by a loop or hairpin region. siRNAs are constituted by a short antisense sequence (19 to 25 nucleotides) followed by a loop of 5-9 nucleotides, and the sense strand. shRNAs may be encoded by plasmids or virus, particularly retrovirus and, more particularly, retrovirus and under the control of promoters such as U6 promoter for RNA polymerase III.

The siRNAs of the invention are substantially homologous to type 1 or type 2 5-HTR mRNA or this protein-coding genome sequence. The term "substantially honomogous" is understood to mean that siRNAs have a sequence sufficiently complementary or similar to target mRNA so that siRNA may be able to provoke mRNA degradation by RNA interference. Suitable siRNAs to provoke interference include siRNAs formed by RNA, as well as siRNAs containing chemically different modifications such as:

siRNAs in which the links between nucleotides are different from those appearing in nature, such as phosphorothioate links.

Stranded-RNA conjugates with a functional reagent, such as a fluorophoro.

Modification of the ends of RNA strands, particularly the 3' end by the combination with different functional hydroxyl groups at 2'-position.

Sugar-modified nucleotides such as O-alkylated radicals at 2'-position such as 2'-O-methylribose or 2'-O-fluororibose.

Base-modified nucleotides such as halogenated bases (for example, 5-bromouracil and 5-iodouracil) or alkylated bases (for example, 7-methyl-guanosine).

The siRNAs and shRNAs of the invention may be obtained using a series of techniques known to a person skilled in the art. For example, siRNA may be chemically synthesized from protected ribonucleoside phosphoramidites in a conventional DNA/RNA synthesizer. Alternatively, siRNA may be produced by recombinant dicer from plasmid and viral vectors, where the coding region of siRNA strand or strands is under operative control of RNA polymerase III promoters. RNase Dicer processes shRNA into siRNA in cells.

The region which is taken as a basis for the design of siRNA is not limitative and may contain a region of coding sequence (between the initiation codon and the termination codon) or, alternatively, may contain sequences from the 5' or 3' untranslated region, preferably from 25 to 50 nucleotides in length and in any position in 3' position with regard to the initiation codon. A procedure for siRNA design involves the identification of sequence motive AA(N19)TT wherein N may be any nucleotide in the sequence of interest and the selection of those that exhibit a high content in G/C. If said sequence motive is not found, it is possible to identify sequence motive NA(N21) wherein N may be any nucleotide.

In another embodiment, the inhibitor of the invention is an antisense oligonucleotide specific to type 1 5-HTR and/or type 2 5-HTR 1, i.e., molecules whose sequence is complementary to mRNA coding for type 1 5-HTR or type 2 5-HTR, i.e., complementary to cDNA coding strand. The antisense oligonucleotide may be complementary to a complete coding region or a region of same including both the coding region and the 5' and 3' untranslated regions. The antisense oligonucleotides may consist of 5, 10, 15, 20, 25, 30, 35, 40, 45, 50 or more nucleotides in length. The antisense oligonucleotides may be obtained by chemical synthesis or by enzymatic binding reactions widely known to a person skilled in the art. For example, an antisense oligonucleotide may further contain modified nucleotides which increase its biological stability or the stability of the bicatenary DNA-RNA complexes formed between the antisense oligonucleotide and the target polynucleotide, such as phosphorothioate derivatives, peptide nucleic acids and acridine-substituted oligonucleotides. Modified oligonucleotides that may be used for the preparation of antisense nucleic acids include 5-fluorouracil, 5-bromouracil, 5-chlorouracil, 5-iodouracil, hypoxanthine, xanthine, 4-acetyl-citosine, 5-(carboxyhydroxymethyl) uracil, 5-carboxymethylaminomethyl-2-thiouridine, 5-carboxymethylaminomethyl uracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcitosine, 5-methylcitosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocitosine, 5-methyl-2-thiouracil, 2-thiouracil, 4-thiouracil, 5-methyluracil, uracil-5-oxyacetic acid methyl ester, 3-(3-amino-3-N-2-carboxypropyl)uracil, and 2,6-diaminopurine. Alternatively, the antisense nucleic acid may be produced biologically using an expression vector in which the antisense-oriented nucleic acid has been cloned.

Another group of inhibitors that can be used in the present invention are catalytically active nucleic acids known as ribozymes. Ribozymes comprise a catalytic region and a second region whose sequence is complementary to target nucleic acid and confers substrate specificity on the ribozime. After the interaction between the ribozime and its substrate by hybridization and coupling between complementary regions of target nucleic acid and ribozime, an activation of the catalytic region is produced provoking the inter- or intramolecular rupture of target nucleic acid. Basic considerations for the design of ribozimes are widely known to a person skilled in the art (see, for example, Doherty and Doudna (Annu. Rev. Biophys. Biomol. Struct. 2001; 30:457-75).

Other compounds capable of inhibiting type 1 5-HTR or type 2 5-HTR expression that can be used in the invention include aptamers and spiegelmers. Aptamers and spiegelmers are single-stranded or double-stranded D- or L-nucleic acids that specifically bind to the protein resulting in a modification of the biological activity of the protein. Aptamers and spiegelmers are 15 to 80 nucleotides in length and, preferably, 20 to 50 nucleotides in length.

Suitable methods for determining whether an inhibitor is capable of decreasing mRNA levels include, without limitation, standard assays for determining mRNA expression levels such as qPCR, RT-PCR, RNA protection analysis, Northern blot, RNA dot blot, in situ hybridization, microarray technology, tag based methods such as serial analysis of gene expression (SAGE) including variants such as Long-SAGE and SuperSAGE, microarrays, fluorescence in situ hybridization (FISH), including variants such as Flow-FISH, qFiSH and double fusion FISH (D-FISH), and the like.

Suitable methods for determining whether an inhibitor acts by decreasing the type 1 or type 2 5-HTR protein levels include the quantification by means of conventional methods, for example, using antibodies with a capacity to specifically bind to the proteins encoded by the gene (or to fragments thereof containing antigenic determinants) and subsequent quantification of the resulting antibody-antigen complexes.

An inhibitor of the invention may inhibit type 1 or type 2 5-HTR activity by at least 5%, at least 10%, at least 25%, at least 50%, at least 75%, or at least 90%, and all ranges between 5% and 100%. Suitable methods for determining whether an inhibitor acts by decreasing the type1 or type 2 5-HTR activity have been previously described.

In another preferred embodiment the inhibitor is a type 1 5-HTR inhibitor, preferably an antagonist.

According to the invention, the serotonin receptor (5-HTR) inhibitor selected from the group consisting of a type 1 5-HTR inhibitor and a type 2 5-HTR inhibitor is useful for preventing and/or treating a subject suffering a haematological malignancy. In a preferred embodiment of the invention, the subject is a mammal. In a more preferred embodiment of the invention, the subject is a human of any race and sex. In another preferred embodiment, the haematological malignancy is leukaemia, more preferred acute myeloid leukaemia (AML).

As the skilled person acknowledges, effectiveness of a type 1 5-HTR inhibitor and a type 2 5-HTR inhibitor in a haematological malignancy therapy may be demonstrated by analyzing the haematological response (measure the numbers of white cells, red cells and platelets and the levels of hemoglobin and hematocrit), cytogenetic response and/or serological tumor markers.

Even though individual needs vary, determination of optimal ranges for therapeutically effective amounts of the inhibitor for use according to the invention belongs to the common experience of those experts in the art. In general, the dosage needed to provide an effective treatment, which can be adjusted by one expert in the art, will vary depending on age, health, fitness, sex, diet, weight, degree of alteration of the receptor, frequency of treatment, nature and condition of the injury, nature and extent of impairment or illness, medical condition of the subject, route of administration, pharmacological considerations such as activity, efficacy, pharmacokinetic and toxicology profile of the particular compound used, if using a system drug delivery, and if the inhibitor is administered as part of a combination of drugs.

The inhibitor of the invention may be administered by any suitable administration route, such as, but not limited to, parenteral, oral, topical, nasal, rectal route. In a particular embodiment, the inhibitor described herein is administered by parenteral route, e.g. by intravenous, intrathecal, intraperitoneal, subcutaneous, intradermal, intramuscular or epidural administration.

2—Method for the Identification of a Malignant Cell from a Haematological Malignancy The inventors of the present invention have found that malignant cells from a haematological malignancy, particularly from AML, express type 1 5-HTR and/or type 2 5-HTR in a significantly higher quantity compared to healthy donors. Therefore, the detection of the expression of type 1 5-HTR and/or type 2 5-HTR in blood cells can be useful for identifying malignant cells from a haematological malignancy.

In another aspect, the invention relates to an in vitro method for the identification of a malignant cell from a haematological malignancy in a sample selected from the group consisting of bone marrow, blood and lymph nodes, said method comprising detecting the expression of type 1 5-HTR and/or type 2 5-HTR in said cell.

As a person skilled in the art can know, the expression of type 1 5-HTR and/or type 2 5-HTR can also be detected by detecting the expression of a functionally equivalent variant of said receptors.

"Functionally equivalent variant" is understood to mean all those proteins derived from type 1 5-HTR or type 2 5-HTR sequence by modification, insertion and/or deletion or one or more amino acids, whenever the function is substantially maintained.

The activity of type 1 5-HTR can be determined by detecting decreasing levels of cAMP and increasing levels of phospho-Akt; and the activity of type 2 5-HTR can be determined by detecting increasing levels of IP3 and DAG and also increasing levels of phosphor-ERK1/2.

Preferably, variants of type 1 5-HTR and/or type 2 5-HTR are (i) polypeptides in which one or more amino acid residues are substituted by a preserved or non-preserved amino acid residue (preferably a preserved amino acid residue) and such substituted amino acid may be coded or not by the genetic code, (ii) polypeptides in which there is one or more modified amino acid residues, for example, residues modified by substituent bonding, (iii) polypeptides resulting from alternative processing of a similar mRNA, (iv) polypeptide fragments and/or (v) polypeptides resulting from type 1 5-HTR and/or type 2 5-HTR fusion or the polypeptide defined in (i) to (iii) with another polypeptide, such as a secretory leader sequence or a sequence being used for purification (for example, His tag) or for detection (for example, Sv5 epitope tag). The fragments include polypeptides generated through proteolytic cut (including multisite proteolysis) of an original sequence. The variants may be post-translationally or chemically modified. Such variants are supposed to be apparent to those skilled in the art.

As known in the art, the "similarity" between two polypeptides is determined by comparing the amino acid sequence and the substituted amino acids preserved from a polypeptide with the sequence of a second polypeptide. The variants are defined to include polypeptide sequences different from the original sequence, preferably different from the original sequence in less than 40% of residues per segment concerned, more preferably different from the original sequence in less than 25% of residues per segment concerned, more preferably different from the original sequence in less than 10% of residues per segment concerned, more preferably different from the original sequence in only a few residues per segment concerned and, at the same time, sufficiently homologous to the original sequence to preserve functionality of the original sequence. The present invention includes amino acid sequences which are at least 60%, 65%, 70%, 72%, 74%, 76%, 78%, 80%, 90%, or 95% similar or identical to the original amino acid sequence. The degree of identity between two polypeptides may be determined using computer algorithms and methods which are widely known to those skilled in the art. The identity between two amino acid sequences is preferentially determined using BLASTP algorithm [BLASTManual, Altschul, S. et al., NCBI NLM NIH Bethesda, Md. 20894, Altschul, S., et al., J. Mol. Biol. 215: 403-410 (1990)].

The expression level of type 1 5-HTR and/or type 2 5-HTR are determined in a sample selected from the group consisting of bone marrow, blood and lymph nodes.

A sample from a bone marrow can be obtained by aspiration and trephine biopsy as known in the art. Blood samples can be obtained by conventional methods, using processes known in the state of the art by the person skilled in the art, such as blood extraction by means of puncturing an artery or vein, normally a vein from the inner part of the elbow or from the back of the hand, the blood sample being collected in an air-tight vial or syringe. Lymph nodes are obtained by biopsy of all or part of a lymph node (excisional lymph node biopsy or incisional lymph node biopsy).

The expression "detecting the expression" refers to detecting the presence of a haematological cell in a sample carrying a type 1 5-HTR and/or a type 2 5-HTR on its surface or expressing type 1 5-HTR and/or type 2 5-HTR mRNA. Said detection may be qualitative or quantitative.

In an embodiment the method for identifying a malignant cell of the present invention does not require the determination of the level of expression of type 1 5-HTR and/or type 2 5-HTR.

In another embodiment, the method for identifying a malignant cell of the present invention comprises determining the expression level of type 1 5-HTR and/or type 2 5-HTR.

The expression "determining the expression level", as used herein, refers to determining the level of expression of a biomarker (type 1 5-HTR and/or type 2 5-HTR) and/or the number of cells carrying this biomarker on its surface (i.e. a cell surface marker). Therein, the level of expression refers to the level of mRNA and/or the level of protein and/or the number of cells carrying a biomarker on its surface.

Methods for detecting the expression can be based on detecting type 1 5-HTR and/or type 2 5-HTR mRNA or protein, or they also can be based on determining the mRNA levels or protein levels and the levels of variants thereof, in a sample as a whole, in cells of a sample and/or in the non-cellular fraction of a sample.

Methods for detecting mRNA are well known in the art and include, e.g., real-time PCR (rtPCR), northern blotting, nanostring and microarray technologies.

By way of a non-limiting illustration, the expression levels are determined by means of the quantification of the levels of mRNA encoded by said genes. The latter can be quantified by means of using conventional methods, for example, methods comprising the amplification of mRNA and the quantification of the amplification product of said mRNA, such as electrophoresis and staining, or alternatively, by means of Northern blot and the use of suitable probes of the mRNA of the gene of interest or of its corresponding cDNA/cRNA, mapping with the Si nuclease, RT-PCR, hybridization, microarrays, etc. Similarly, the levels of the cDNA/cRNA corresponding to said mRNA encoded by the marker gene can also be quantified by means of using conventional techniques; in this event, the method of the invention includes a step of synthesis of the corresponding cDNA by means of reverse transcription (RT) of the corresponding mRNA followed by the synthesis (RNA polymerase) and amplification of the cRNA complementary to said cDNA.

In order to normalize the values of mRNA expression among the different samples, it is possible to compare the expression levels of the mRNA of interest in the test samples with the expression of a control RNA. A "control RNA", as used herein, relates to RNA whose expression levels do not change or change only in limited amounts. Preferably, the control RNA is mRNA derived from housekeeping genes and which code for proteins which are constitutively expressed and carry out essential cellular functions. Preferred housekeeping genes for use in the present invention include 18-S ribosomal protein, β-2-microglobulin, ubiquitin, cyclophilin, GAPDH, PSMB4, tubulin and β-actin.

Alternatively, it is also possible to determine the expression levels of the type 1 5-HTR and/or type 2 5-HTR genes by means of the determination of the expression levels of the proteins encoded by said genes, since if the expression of genes is increased, an increase of the amount of corresponding proteins should occur and if the expression of genes is decreased, a decrease of the amount of corresponding proteins should occur.

Virtually any conventional method can be used within the frame of the invention to detect and quantify the levels of proteins. By way of a non-limiting illustration, the expression levels are determined by means of antibodies with the capacity for binding specifically to the protein to be determined (or to fragments thereof containing the antigenic determinants) and subsequent quantification of the resulting antigen-antibody complexes. The antibodies that are going to be used in this type of assay can be, for example, polyclonal sera, hybridoma supernatants or monoclonal antibodies, antibody fragments, Fv, Fab, Fab' and F(ab')2, scFv, diabodies, triabodies, tetrabodies and humanized antibodies. At the same time, the antibodies may or may not be labeled. Illustrative, but non-exclusive, examples of markers that can be used include radioactive isotopes, enzymes, fluorophores, chemoluminescent reagents, enzyme cofactors or substrates, enzyme inhibitors, particles, dyes, etc. There is a wide variety of well-known assays that can be used in the present invention, using non-labeled antibodies (primary antibody), labeled antibodies (secondary antibodies) or labeled antagonists or agonists of type 1 or 2 5-HTR; these techniques include Western-blot or immunoblot, ELISA (enzyme-linked immunosorbent assay), RIA (radioimmunoassay), competitive EIA (enzyme immunoassay), DAS-ELISA (double antibody sandwich ELISA), immunocytochemical and immunohistochemical techniques, immunofluorescence, techniques based on the use of biochips or protein microarrays including specific antibodies or assays based on the colloidal precipitation in formats such as reagent strips. Other forms of detecting and quantifying the proteins include affinity chromatography techniques, ligand-binding assays, etc.

In a preferred embodiment of the invention, the type 1 5-HTR and/or type 2 5-HTR-expressing cells are detected by immunocytochemistry, preferably by immunofluorescence.

In a preferred embodiment of the invention, detecting the expression or determining the levels of type 1 5-HTR and/or type 2 5-HTR is performed by immunofluorescence. Immunofluorescence (IF) is a technique used for light microscopy with a fluorescence microscope and is used primarily on biological samples. This technique uses the specificity of antibodies to their antigen to target fluorescent dyes to specific biomolecule targets within a cell, and therefore allows visualisation of the distribution of the target molecule through the sample. IF is a widely used example of immunostaining and is a specific example of immunohisto-chemistry (IHC) or immunocytochemistry (ICC) that makes use of fluorophores to visualise the location of the antibodies. IF can be used on tissue sections, cultured cell lines, or individual cells. IF can be used in combination with other, non-antibody methods of fluorescent staining, for example, use of DAPI to label DNA. Several microscope designs can be used for analysis of IF samples; the simplest is the epifluorescence microscope, and the confocal microscope is also widely used. Various super-resolution microscope designs that are capable of much higher resolution can also be used. In a preferred embodiment, the identification of a malignant cell is performed by flow cytometry, which is a laser-based, biophysical technology employed in cell counting, cell sorting and biomarker detection by suspending cells in a stream of fluid and passing them by an electronic detector.

According to the invention, the detection of the expression of type 1 5-HTR and/or type 2 5-HTR in a sample selected from the group consisting of bone marrow, blood and lymph nodes is useful for the identification of a malignant cell from a haematological malignancy.

In a preferred embodiment, the blood sample is peripheral blood.

In another preferred embodiment, the type 1 5-HTR is 5-HTR 1A and the type 2 5-HTR is selected from the group consisting of 5-HTR 2A, 5-HTR 2B and 5-HTR 2C. In a more preferred embodiment, the type 2 5-HTR is 5-HTR 2C.

In another preferred embodiment, the method of the invention for identifying a malignant cell comprises detecting the expression of 5-HTR1A and 5-HTR2C.

In a preferred embodiment, the haematological malignancy is leukaemia, more preferably acute myeloid leukaemia.

All the terms and embodiments previously described are equally applicable to this aspect of the invention.

3—Method for Diagnosing a Haematological Malignancy

In another aspect, the invention relates to an vitro method for diagnosing a haematological malignancy in a subject which comprises identifying malignant cells by a method according to the invention, particularly identification of a malignant cell from a haematological malignancy in a sample selected from the group consisting of bone marrow, blood and lymph nodes, said method comprising detecting the expression of type 1 5-HTR and/or type 2 5-HTR in said cell.

Diagnosing, as used herein, refers both to the process of attempting to determine and/or identify a possible disease in a subject, i.e. the diagnostic procedure, and to the opinion reached by this process, i.e. the diagnostic opinion. As such, it can also be regarded as an attempt at classification of an individual's condition into separate and distinct categories that allow medical decisions about treatment and prognosis to be made. As will be understood by those skilled in the art, the diagnosis of a haematological malignancy, although preferred to be, need not be correct for 100% of the subjects to be diagnosed or evaluated. The term, however, requires that a statistically significant portion of subjects can be identified as suffering from a haematological malignancy. Whether a subject is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90%, or at least 95%. The p-values are, preferably, 0.05, 0.01, 0.005 or lower.

In a preferred embodiment, the method for diagnosing a haematological malignancy in a subject comprises:
 (a) determining the levels of type 1 5-HTR and/or type 2 5-HTR-expressing cells in a sample from said subject selected from the group consisting of bone marrow, blood and lymph nodes, and
 (b) comparing said levels with a reference value
wherein increased levels of type 1 5-HTR and/or type 2 5-HTR-expressing cells with respect to the reference value are indicative of the subject suffering from a haematological malignancy.

The reference value derives from a sample collection formed preferably by a mixture of the sample to be analyzed from normal individuals not affected by a haematological malignancy. Said reference value can be determined by means of techniques well known in the state of the art, for example, determining the mean of the levels of type 1 5-HTR and/or type 2 5-HTR proteins measured in a sample taken from healthy subjects. The reference value can also be obtained from the constitutively expressed proteins taken from the same subject to be analyzed.

In a preferred embodiment, the blood sample is peripheral blood. In another preferred embodiment, the type 1 5-HTR is 5-HTR 1A and the type 2 5-HTR is selected from the group consisting of 5-HTR 2A, 5-HTR 2B and 5-HTR 2C. In a more preferred embodiment, the type 2 5-HTR is 5-HTR 2C.

In another preferred embodiment, the method for diagnosing a haematological malignancy of the invention comprises detecting the expression of 5-HTR 1A and 5-HTR 2C.

In a preferred embodiment, the haematological malignancy is leukaemia, more preferably acute myeloid leukaemia.

In another preferred embodiment, the type 1 5-HTR and/or type 2 5-HTR-expressing cells are detected by immunocytochemistry, preferably by immunofluorescence, more preferred by flow cytometry.

All the terms and embodiments previously described are equally applicable to this aspect of the invention.

4—Method for the Isolation of a Malignant Cell

In another aspect, the invention relates to an in vitro method for the isolation of a malignant cell from a haematological malignancy in a sample selected from the group consisting of bone marrow, blood and lymph nodes, said method comprising detecting the expression of type 1 5-HTR and/or type 2 5-HTR in said cell and isolating said cell expressing said 5-HTR.

The term "isolating", as used herein, means identifying and separating or removing a malignant cell from the remaining components present in a sample selected from the group consisting of bone marrow, blood and lymph nodes.

In a preferred embodiment, the blood sample is peripheral blood.

In another preferred embodiment, the type 1 5-HTR is 5-HTR 1A and the type 2 5-HTR is selected from the group consisting of 5-HTR 2A, 5-HTR 2B and 5-HTR 2C. In a more preferred embodiment, the type 2 5-HTR is 5-HTR 2C.

In another preferred embodiment, the method of the invention for isolating a malignant cell comprises detecting the expression of 5-HTR 1A and 5-HTR 2C.

In a preferred embodiment, the haematological malignancy is leukaemia, more preferably acute myeloid leukaemia.

In another preferred embodiment, the type 1 5-HTR and/or type 2 5-HTR-expressing cells are detected by immunocytochemistry, preferably by immunofluorescence, more preferred by flow cytometry.

All the terms and embodiments previously described are equally applicable to this aspect of the invention.

5—Method for Determining the Prognosis

In another aspect, the invention relates to an in vitro method for determining the prognosis of a subject suffering from a haematological malignancy which comprises:
  (a) determining the expression level of type 1 5-HTR and/or type 2 5-HTR in cells of a sample from said subject selected from the group consisting of bone marrow, blood and lymph nodes, and
  (b) comparing said level with a reference value
wherein a decrease of the expression level of type 1 5-HTR and/or type 2 5-HTR with respect to the reference value is indicative that the subject shows a good prognosis or wherein an increase of the expression level of type 1 5-HTR and/or type 2 5-HTR with respect to the reference value is indicative that the subject shows a bad prognosis In a preferred embodiment, the haematological malignancy is leukaemia, and more preferably acute myeloid leukaemia.

The term "determining", as used herein, relates to the determination of any parameter that can be useful in determining the evolution of a patient. As will be understood by those skilled in the art, the prediction of the outcome, although preferred to be, need not be correct for 100% of the subjects to be diagnosed or evaluated. The term, however, requires that a statistically significant portion of subjects can be identified as having an increased probability of having a given outcome. Whether a subject is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at 90%, or at least 95%. The p-values are, preferably, 0.05, 0.01, 0.005 or lower.

The term "prognosis", as used herein, means the likelihood of recovery from a disease or the prediction of the probable development or outcome of a disease, including but not limited to predicting the length of overall survival (OS), 1 year survival (1YS), response to therapy (RT), disease-free survival, progression-free survival, and event-free survival. As will be understood by those skilled in the art, the prediction, although preferred to be, need not be correct for 100% of the subjects to be diagnosed or evaluated. The term, however, requires that a statistically significant portion of subjects can be identified as having an increased probability of having a given outcome. Whether a subject is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90% at least 95%. The p-values are, preferably 0.05, 0.02, 0.01 or lower.

Standard criteria (Miller, et al. Cancer, 1981; 47(1): 207-14) can be used herewith to evaluate the clinical outcome of a patient in response to a therapy. Any parameter which is widely accepted for determining the efficacy of treatments can be used for determining the clinical outcome of a patient in response to a treatment and include, without limitation:
  disease-free progression which, as used herein, describes the proportion of subjects in complete remission who have had no recurrence of disease during the time period under study.
  disease-free survival (DFS), as used herewith, is understood as the length of time after treatment for a disease during which a subject survives with no sign of the disease.
  objective response which, as used in the present invention, describes the proportion of treated subjects in whom a complete or partial response is observed.
  tumor control which, as used in the present invention, relates to the proportion of treated subjects in whom complete response, partial response, minor response or stable disease≥6 months is observed.
  progression free survival which, as used herein, is defined as the time from start of treatment to the first measurement of cancer growth.
  Time to progression, as used herein, relates to the time after a disease is treated until the disease starts to get worse. The term "progression" has been previously defined.
  six-month progression free survival which, as used herein, relates to the percentage of subjects wherein free of progression in the first six months after the initiation of the therapy.
  Overall survival (OS) which, as used herein, is defined as the percentage of patients who survive after diagnosis of a primary cancer.
  median survival which, as used herein, relates to the time at which half of the subjects enrolled in the study are still alive, and
  Cytogenetic risk stratification, which, as used herein, relates to the probability of 5-year survival based on the chromosome structure of the leukemic cells.

In a preferred embodiment, the clinical outcome of a patient is measured by determining the cytogenetic risk stratification.

The first step of the in vitro method for determining the prognosis, comprises determining the expression level of type 1 5-HTR and/or type 2 5-HTR in cells of a sample from said subject selected from the group consisting of bone marrow, blood and lymph nodes. Determining the level of expression of a biomarker, refers to determining the level of expression of a biomarker and/or the number of cells carrying a biomarker on its surface (i.e. a cell surface marker). Therein, the level of expression refers to the level of mRNA and/or the level of protein and/or the number of cells carrying a biomarker on its surface. Examples of methods for determining the expression level of a biomarker have been previously described.

In another preferred embodiment, the in vitro method for determining the prognosis of a subject suffering from a haematological malignancy comprises determining the expression level of type 1 5-HTR and/or type 2 5-HTR by measuring the level of mRNA encoded by the type 1 5-HTR genes and/or type 2 5-HTR genes, or of variants thereof. In another preferred embodiment, the expression level of type 1 5-HTR and/or type 2 5-HTR is determined by measuring the level of type 1 5-HTR proteins and/or type 2 5-HTR proteins, or of variants thereof. In a more preferred embodiment, the mRNA expression level is determined by PCR. In another preferred embodiment, the expression level of proteins or of variants thereof is determined by Western blot or immunocytochemistry. In a more preferred embodiment, the expression level of type 1 5-HTR and/or type 2 5-HTR is determined by semi-quantitative PCR.

In another preferred embodiment, the blood sample is peripheral blood.

In a preferred embodiment, the in vitro method for determining the prognosis of a subject suffering from a haematological malignancy comprises determining the level of type 1 5-HTR. In a more preferred embodiment, the type 1 5-HTR is selected from the group consisting of 5-HTR 1A and 5-HTR-1B.

In a preferred embodiment, the method comprises determining the expression level of 5-HTR 1A and 5-HTR-1B.

In a second step the in vitro method for determining the prognosis comprises comparing the level of type 1 5-HTR and/or type 2 5-HTR with a reference value. Said comparison allows concluding if the subject shows a good or a bad prognosis.

In a preferred embodiment, the prognosis determined by the in vitro method of the invention is the probability of 5-year survival.

All the terms and embodiments previously described are equally applicable to this aspect of the invention.

6—Method for Monitoring the Effect of a Therapy

In another aspect, the invention relates to an in vitro method for monitoring the effect of a therapy in a subject suffering from a haematological malignancy and being treated with said therapy which comprises:
  a) determining the expression level of type 1 5-HTR and/or type 2 5-HTR in cells of a sample from said subject selected from the group consisting of bone marrow, blood and lymph nodes, and
  b) comparing said level with the expression level of type 1 5-HTR and/or type 2 5-HTR in cells of a sample from said subject at an earlier point of time
wherein a decrease of the expression level of type 1 5-HTR and/or type 2 5-HTR with respect to the level determined in a sample from said subject at an earlier point of time is indicative that the therapy is being effective or wherein an increase of the expression level of type 1 5-HTR and/or type 2 5-HTR with respect to the level determined in a sample from said subject at an earlier point of time is indicative that the therapy is being ineffective.

In a preferred embodiment, the haematological malignancy is leukaemia, and more preferably acute myeloid leukaemia.

As a person skilled in the art understands, the therapy is directed to treating haematological malignancy. By way of non-limitative example a combination of cytarabine (ara-C) and daunorubicin (daunomycin) or idarubicin, fludarabine or topotecan can be used. In another embodiment the therapy is a type 1 5-HTR inhibitor or a type 2 5-HTR inhibitor.

Methods for determining the expression level of type 1 5-HTR and/or type 2 5-HTR have been previously described in detail.

In a preferred embodiment, the in vitro method for monitoring the effect of a therapy in a subject suffering from a haematological malignancy comprises determining the level of type 1 5-HTR. In a more preferred embodiment, the type 1 5-HTR is selected from the group consisting of 5-HTR 1A and 5-HTR-1B.

In a preferred embodiment, the method comprises determining the expression level of 5-HTR 1A and 5-HTR-1B.

In another preferred embodiment, the blood sample is peripheral blood.

In another preferred embodiment, the in vitro method for monitoring the effect of a therapy in a subject suffering from a haematological malignancy comprises determining the expression level of type 1 5-HTR and/or type 2 5-HTR by measuring the level of mRNA encoded by the type 1 5-HTR genes and/or type 2 5-HTR genes, or of variants thereof. In another preferred embodiment, the expression level of type 1 5-HTR and/or type 2 5-HTR is determined by measuring the level of type 1 5-HTR proteins and/or type 2 5-HTR proteins, or of variants thereof.

In a more preferred embodiment, the mRNA expression level is determined by PCR. In another preferred embodiment, the expression level of proteins or of variants thereof is determined by Western blot or immunocytochemistry. In a more preferred embodiment, the expression level of type 1 5-HTR and/or type 2 5-HTR is determined by semi-quantitative PCR.

All the terms and embodiments previously described are equally applicable to this aspect of the invention.

7—Method for Designing a Customized Therapy

In another aspect, the invention relates to an in vitro method for designing a customized therapy for a subject diagnosed with a haematological malignancy which comprises
  a) determining the levels of the type 1 5-HTR and/or type 2 5-HTR-expressing cells in a sample from said subject selected from the group consisting of bone marrow, blood and lymph nodes, and
  b) comparing said levels with a reference value
wherein increased levels of type 1 5-HTR and/or type 2 5-HTR-expressing cells with respect to the reference value are indicative that the subject is to be treated with a type 1 5-HTR inhibitor and/or a type 2 5-HTR inhibitor.

Designing a customized therapy to a subject diagnosed with a haematological malignancy is understood as deciding, based on expression of type 1 5-HTR and/or type 2 5-HTR, administering as appropriate a type 1 5-HTR inhibitor and/or a type 2 5-HTR inhibitor.

In a preferred embodiment the 5-HTR inhibitor is selected from a compound of Table 1 or a pharmaceutically salt thereof.

In a more preferred embodiment, the 5-HTR inhibitor is selected from the group consisting of apomorphine methiothepin, amperozide and a pharmaceutically acceptable salt thereof.

In a preferred embodiment, the in vitro method for designing a customized therapy in a subject suffering from a haematological malignancy comprises determining the expression level of type 1 5-HTR. In a more preferred embodiment, the type 1 5-HTR is selected from the group consisting of 5-HTR 1A and 5-HTR-1B.

In a preferred embodiment, the method comprises determining the expression level of 5-HTR 1A and 5-HTR 1B.

In another preferred embodiment, the haematological malignancy is leukaemia, and more preferably acute myeloid leukaemia.

In another preferred embodiment, the blood sample is peripheral blood.

In another preferred embodiment, the in vitro method for monitoring the effect of a therapy in a subject suffering from a haematological malignancy comprises determining the expression level of type 1 5-HTR and/or type 2 5-HTR by measuring the level of mRNA encoded by the type 1 5-HTR genes and/or type 2 5-HTR genes, or of variants thereof. In another preferred embodiment, the expression level of type 1 5-HTR and/or type 2 5-HTR is determined by measuring the level of type 1 5-HTR proteins and/or type 2 5-HTR proteins, or of variants thereof. In a more preferred embodiment, the mRNA expression level is determined by PCR. In another preferred embodiment, the expression level of proteins or of variants thereof is determined by Western blot or immunocytochemistry. In a more preferred embodiment, the expression level of type 1 5-HTR and/or type 2 5-HTR is determined by semi-quantitative PCR.

All the terms and embodiments previously described are equally applicable to this aspect of the invention.

The invention will be described by way of the following examples which are to be considered as merely illustrative and not limitative of the scope of the invention.

EXAMPLES

Material and Methods

Example 1

Figure 1:
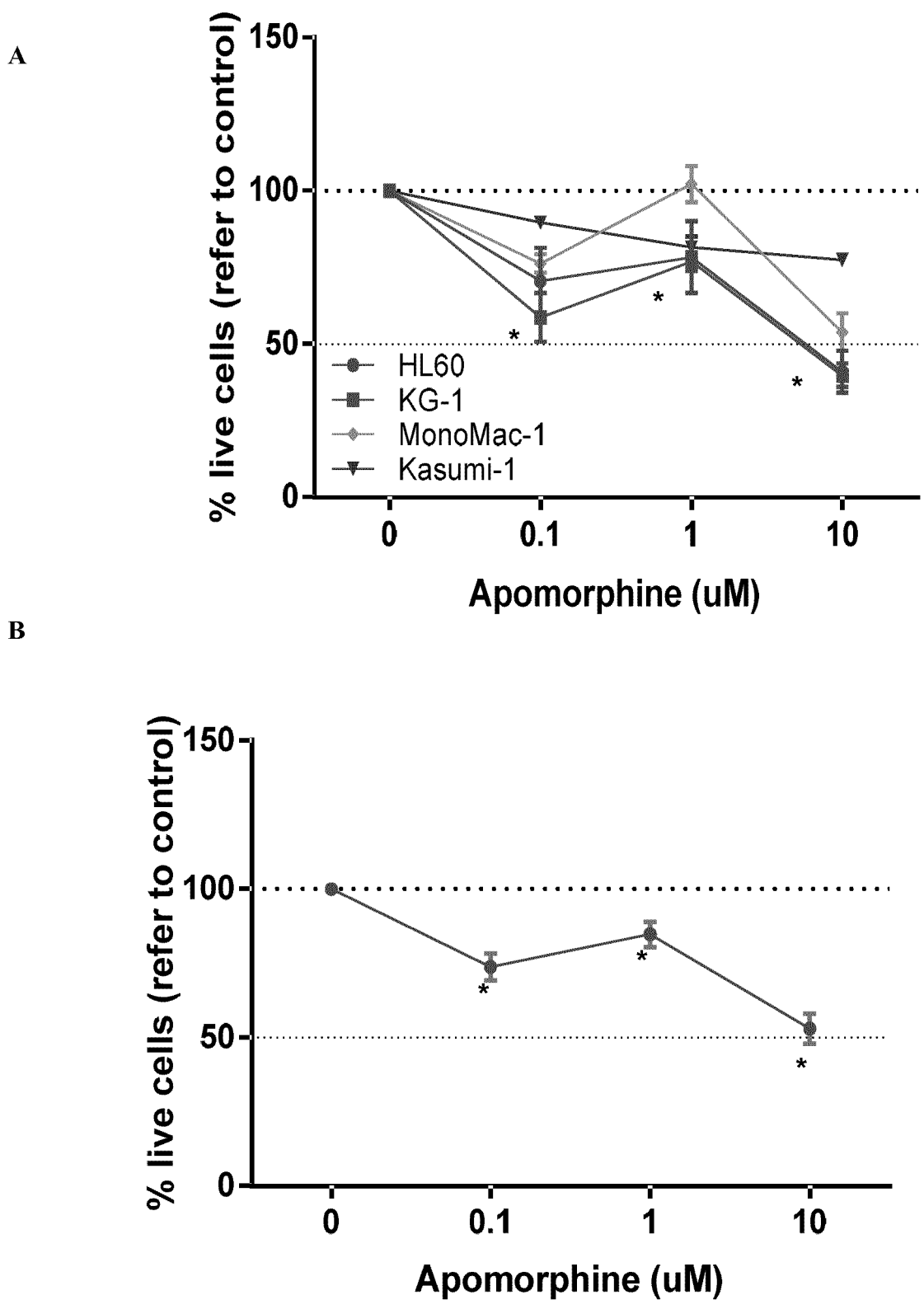
FIG. 1. Apomorphine treatment reduced AML cell viability. $10^6$ HL-60, KG-1, MonoMac-1 and Kasumi-1 cells per mL in complete RPMI media were treated with 0.1, 1 and 10 µM Apomorphine for 72 h. Cells were incubated at 37° C. and 5% $CO_2$. Cells were stained with 7-aminoactinomycin D (7-AAD, CAS no. 7240-37-1) and Hoechst 33342 (CAS no. 23491-52-3) and analyzed by flow cytometry. Nuclear cells were identified by Hoechst positive staining, while death cells were excluded by 7-AAD positive staining. Cell number was calculated by volumetric count. A. The mean (symbol) for each AML cell line and standard deviation (error bars) from 6 different biological replicates are represented. B. The average corresponding to the four different AML cell lines is represented. $*p<0.05$.

Serotonin Receptor (5HTR) Antagonists Type 1 and 2 have a Cytotoxic Effect on AML Cell Lines In order to test the anti-leukaemic effect of 5HTR antagonists, HL-60 (Collins, Gallo et al. Nature. 1977; 270(5635): 347-9), MonoMac-1 (Steube, Teepe et al. Leuk Res. 1997; 21(4):327-35), KG-1 (Koeffler and Golde. Science. 1978; 200(4346):1153-4) and Kasumi-1 (Asou, Tashiro et al. Blood. 1991; 77(9):2031-6) AML (Acute Myeloid Leukaemia) cell lines were treated with the broad 5HTR antagonist Apomorphine (CAS no. 314-19-2) at different doses for 72 h. One million cells per mL were seeded in complete RPMI media supplemented with 10% fetal bovine serum in a 96-well plate. The concentration used for the Apomorphine treatment was 0.1, 1 and 10 µM. As shown in FIG. 1, a reduction in cell viability was detected in a dose-response fashion in all AML cell lines tested.

Figure 2:
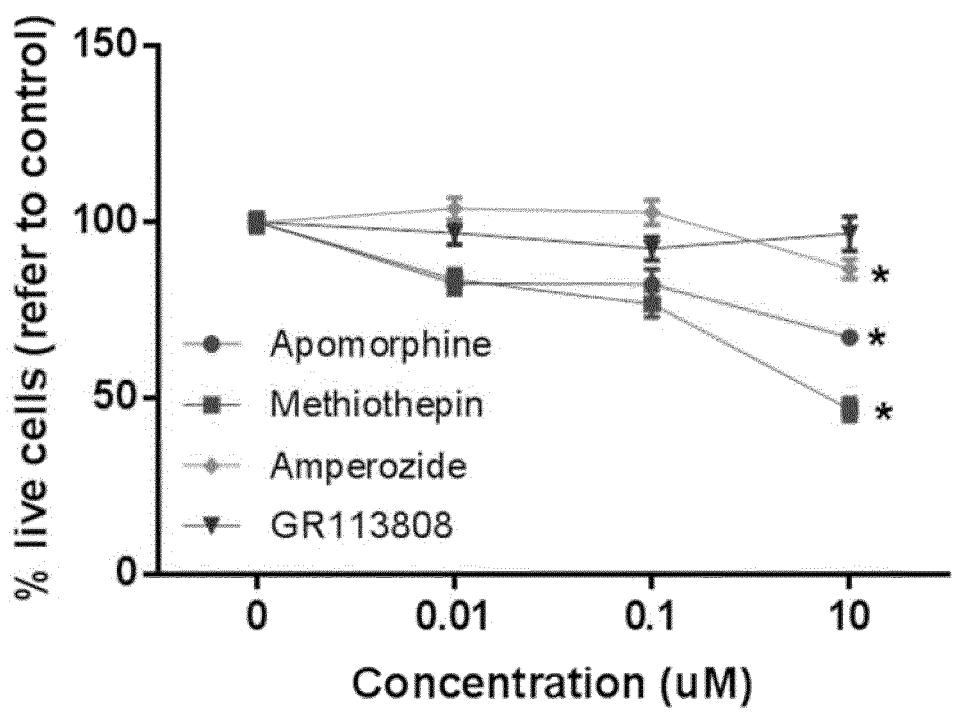
FIG. 2. Type 1 and 2 5HTR antagonists induced cell death on AML cell lines. $10^6$ HL-60, KG-1, MonoMac-1 and Kasumi-1 AML cell lines per mL were incubated with Apomorphine, Methiothepin, Amperozide or GR113808 at 0.1, 1 and 10 µM for 72 h at 37° C. and 5% $CO_2$. Nuclear cells were identified by Hoechst positive staining, while death cells were excluded by 7-AAD positive staining. Cell number was calculated by volumetric count. A. The mean (symbol) for each AML cell line and standard deviation (error bars) from 6 different biological replicates are represented. B. AML cell lines were treated with 10 µM Apomorphine or Methiothepin in the presence or absence of 5-CT or 5-HT. $*p<0.05$. Apo: apomorphine; Methio: methiothepine.
Figure 2:
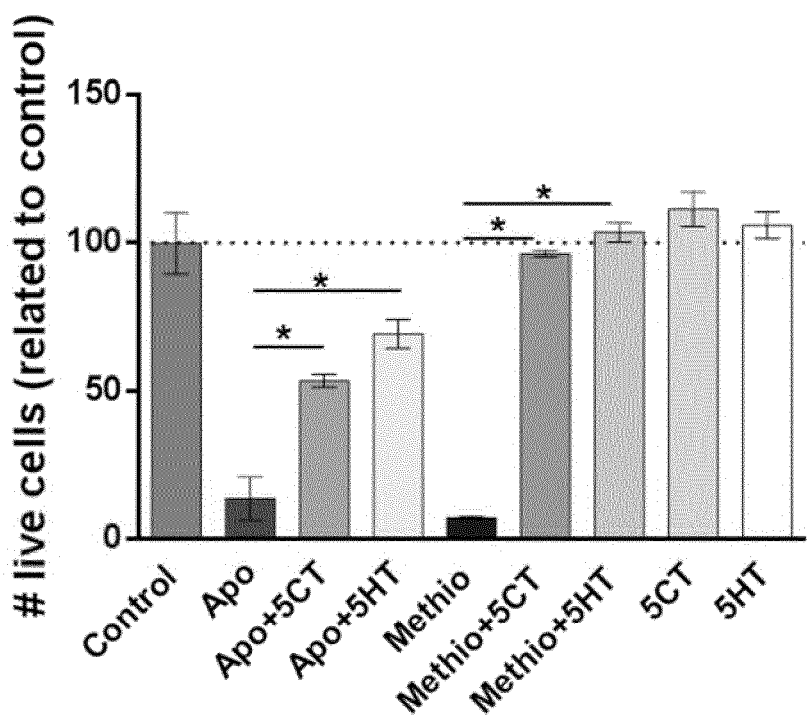

The human 5HTR family is composed by 7 subtypes (from 1 to 7) of receptors (Nichols and Nichols. Chem Rev 2008, 108:16414-41). HL-60, KG-1, MonoMac-1 and Kasumi-1 AML cell lines were incubated with subtype-specific 5HTR antagonists: Apomorphine (type 1, 2 and 5), Methiothepin (type 1 and 2) (CAS no. 74611-28-2), Amperozide (type 2) (CAS no. 75558-90-6), GR113808 (type 4) (CAS no. 144625-51-4). 72 h after treatment, cell viability was determined by flow cytometry. Cells were stained with 7-AAD (CAS no. 7240-37-1) and Hoechst 33342 (CAS no. 23491-52-3). Viability cells were identified by 7-AAD staining exclusion and the presence of Hoechst positive stain. Cell counts were measured by volume. Only Apomorphine, Methiothepin and Amperozide induced cell death on AML cell lines (FIG. 2); therefore, inhibition of 5THR type 1 and 2 has cytotoxic effect on AML cells. In fact, the anti-leukaemic effect was reversed in the presence of a competitive agonist such as the natural ligand 5-HT (CAS no. 153-98-0) or 5-CT (CAS no. 74885-72-6).

Example 2

Figure 3:
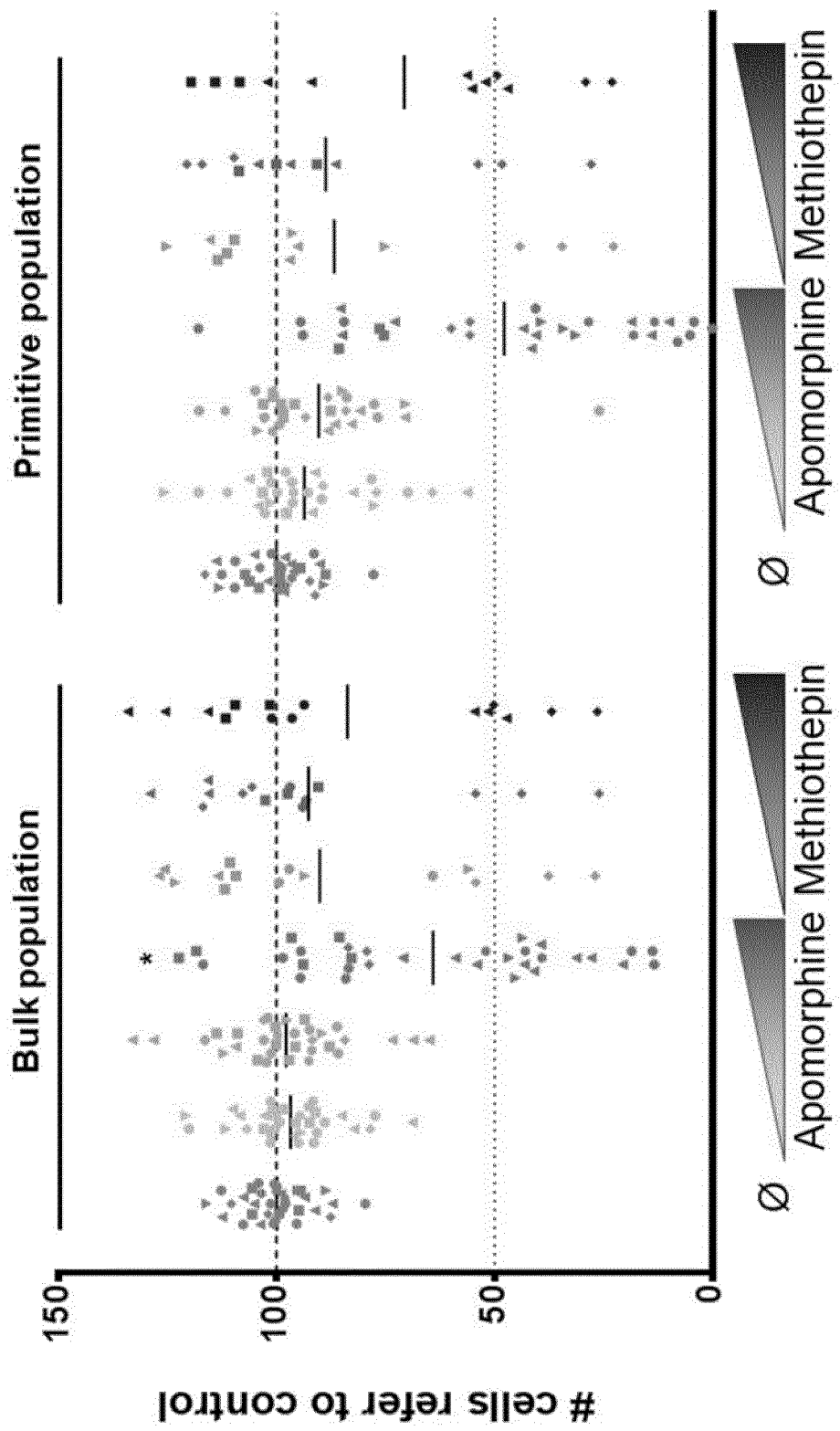
FIG. 3. 5HTR antagonists reduced cell viability of primary patient AML samples at 24 h. $5\times10^6$ primary AML cells per mL were treated with Apomorphine or Methiothepin at 0.1, 1 and 10 µM in complete IMDM media for 24 h at 37° C. and 5% $CO_2$. AML bulk population was identified based on their CD45 expression and SSC profile by cytometry. The primitive AML population was identified within the AML bulk population based on their positivity to CD34 and negativity to CD38. Nuclear cells were identified by Hoechst positive staining, while death cells were excluded by 7-AAD positive staining. Cell number was calculated by volumetric count. 11 primary AML samples were analyzed in triplicates. Each symbol represents a specific AML patient. Bars represent the cell viability mean of each replicate. $*p<0.05$ FIG. 4. 5HTR antagonists reduced cell viability of primary patient AML samples at 72 h. $5\times10^6$ primary AML cells per mL were treated with Apomorphine or Methiothepin at 0.1, 1 and 10 µM in complete IMDM media for 72 h at 37° C. and 5% $CO_2$. AML bulk population was identified based on their CD45 expression and SSC profile by cytometry. The primitive AML population was identified within the AML bulk population based on their positivity to CD34 and negativity to CD38. Nuclear cells were identified by Hoechst positive staining, while death cells were excluded by 7-AAD positive staining. Cell number was calculated by volumetric count. 11 primary AML samples were analyzed in triplicates. Each symbol represents a specific AML patient. Bars represent the cell viability mean of each replicate. $*p<0.05$.
Figure 4:
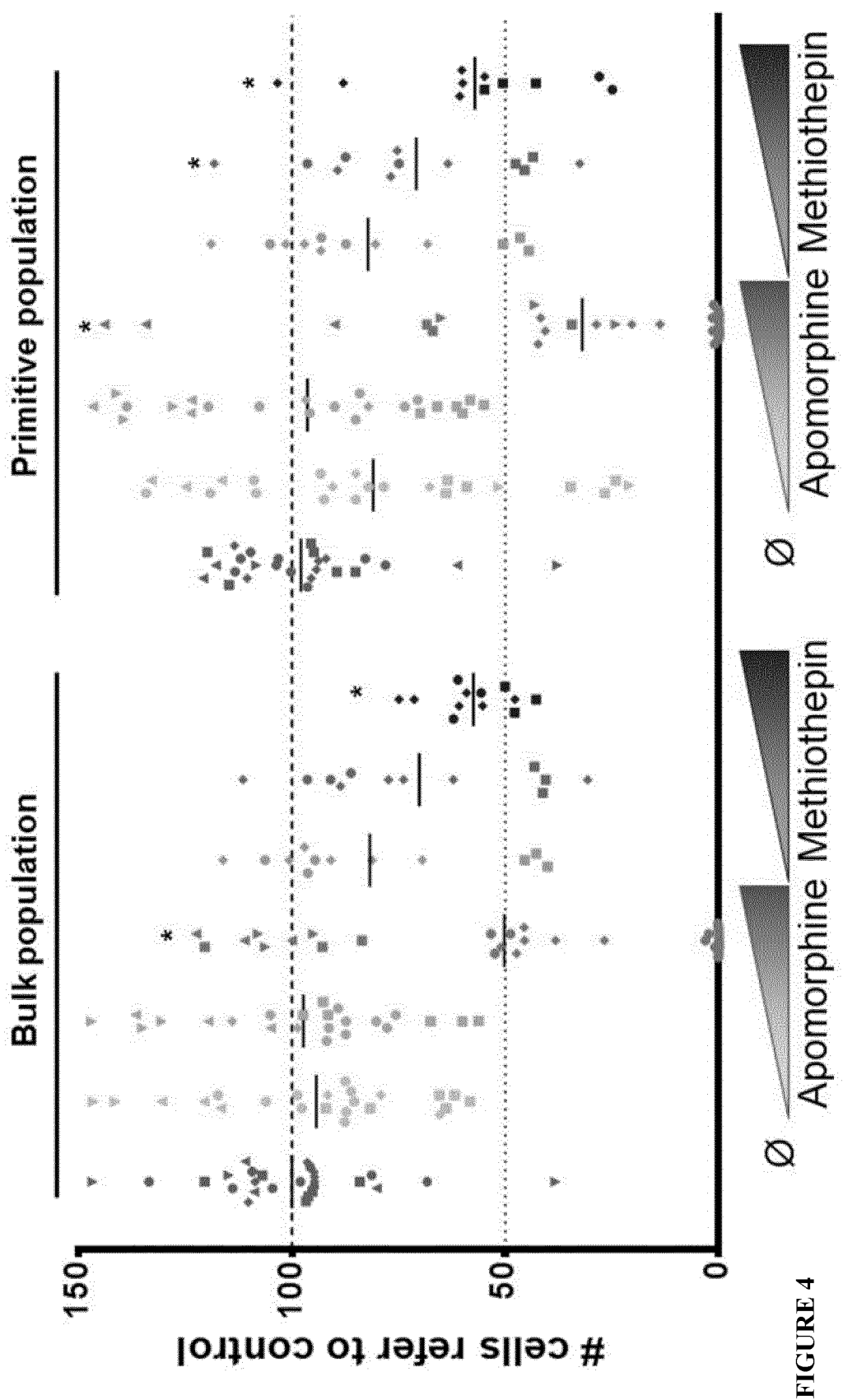

Serotonin Receptor (5HTR) Antagonists Type 1 and 2 have a Cytotoxic Effect on Primary Patient AML Samples Primary AML patient samples were treated with subtype 1 and 2 HTR antagonists for 24 and 72 h at 0.1, 1 and 10 µM. Five hundred thousand cells per mL were seeded in IMDM supplemented with insulin, transferrin, bovine serum albumin, IL3 and non-essential aminoacids. Cell viability was measured by flow cytometry as described above. Similarly to AML cell lines, both apomorphine and methiothepin treatment induced cell death on primary AML blasts in a dose-response fashion (FIGS. 3 and 4).

Like the normal haematopoietic system, AML is thought to be organized as a hierarchy of distinct and functionally heterogeneous classes of cells that is ultimately sustained by a small number of leukaemic stem cells (LSCs) with enhanced self-renewal capacity, impaired differentiation ability, and increase drug resistance (Bonnet and Dick Nat Med. 1997; 3(7):730-7). The LSC population is found enriched inside the CD34+CD38− AML blast population. Apomorphine and methiothepin reduced cell viability of the most primitive LSC-enriched blast population (FIGS. 3 and 4) identified by flow cytometry based on the presence of CD34 and absence of CD38. In fact, the reduction in the primitive fraction was significantly higher than in the bulk population; thus, 5HTR antagonists selectively affect LSCs.

Example 3

5HTR Antagonists Induced Differentiation on AML Cell Lines

Figure 5:
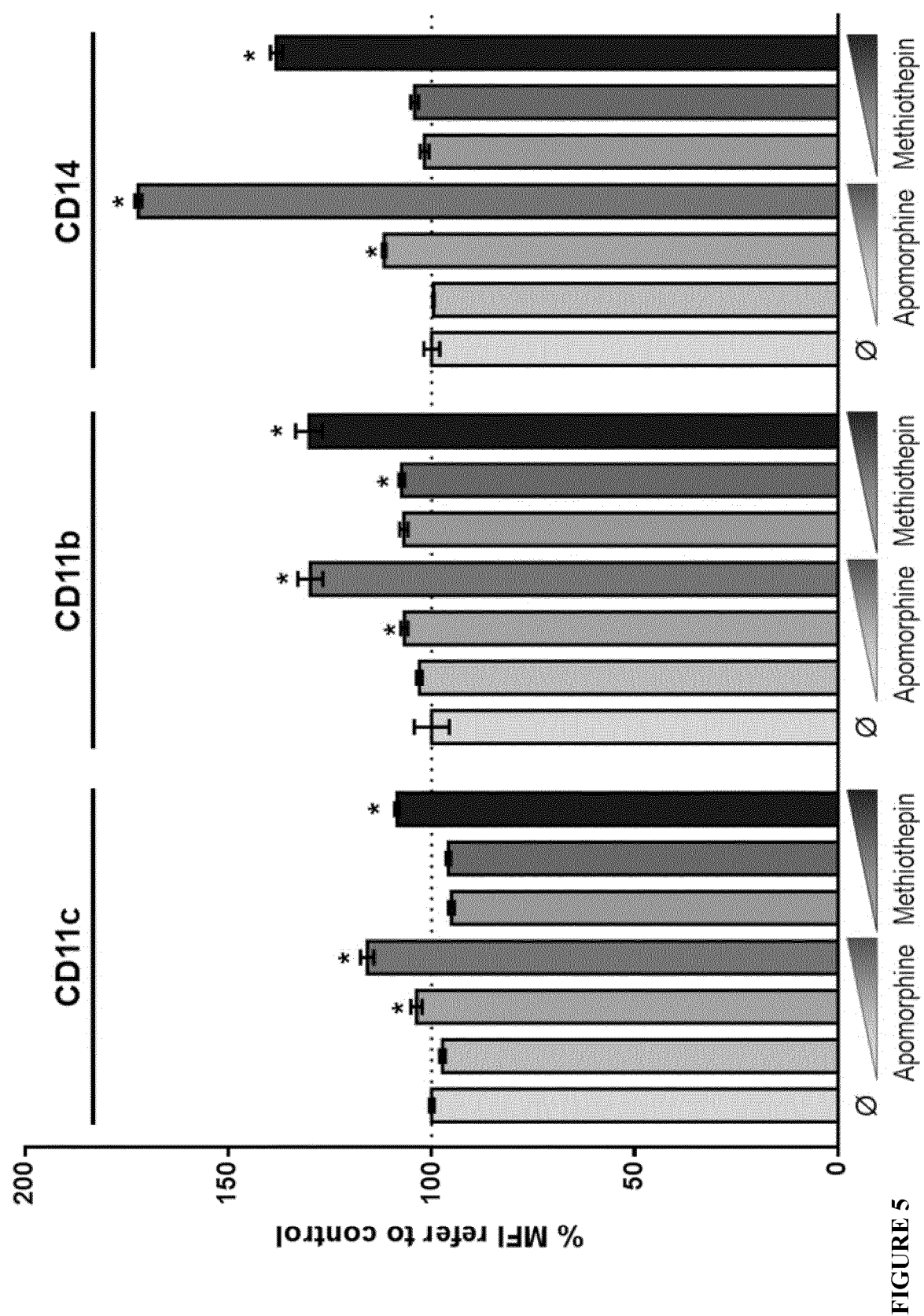
FIG. 5. 5HTR antagonists induced myeloid differentiation on AML cell lines. $10^6$ HL-60, KG-1, MonoMac-1 and Kasumi-1 AML cells per mL were treated with Apomorphine and Methiothepin at 0.1, 1 and 10 µM for 72 h at 37° C. and 5% $CO_2$ in complete RPMI media. The surface expression of CD11c, CD11b and CD14 was detected by flow cytometry. Death cells were excluded by 7-AAD-positive staining. $*p<0.05$. MFI: Mean Fluorescence Intensity.

HL-60, KG-1, MonoMac-1 and Kasumi-1 AML cell lines were treated with Apomorphine and Methiothepin at different concentrations for 72 h as described above. The expression of differentiation-associated surface markers was measured by flow cytometry. In all AML cell lines, the presence of 5HTR antagonists induced the expression of CD11c, CD11b and CD14 (FIG. 5).

Figure 6:
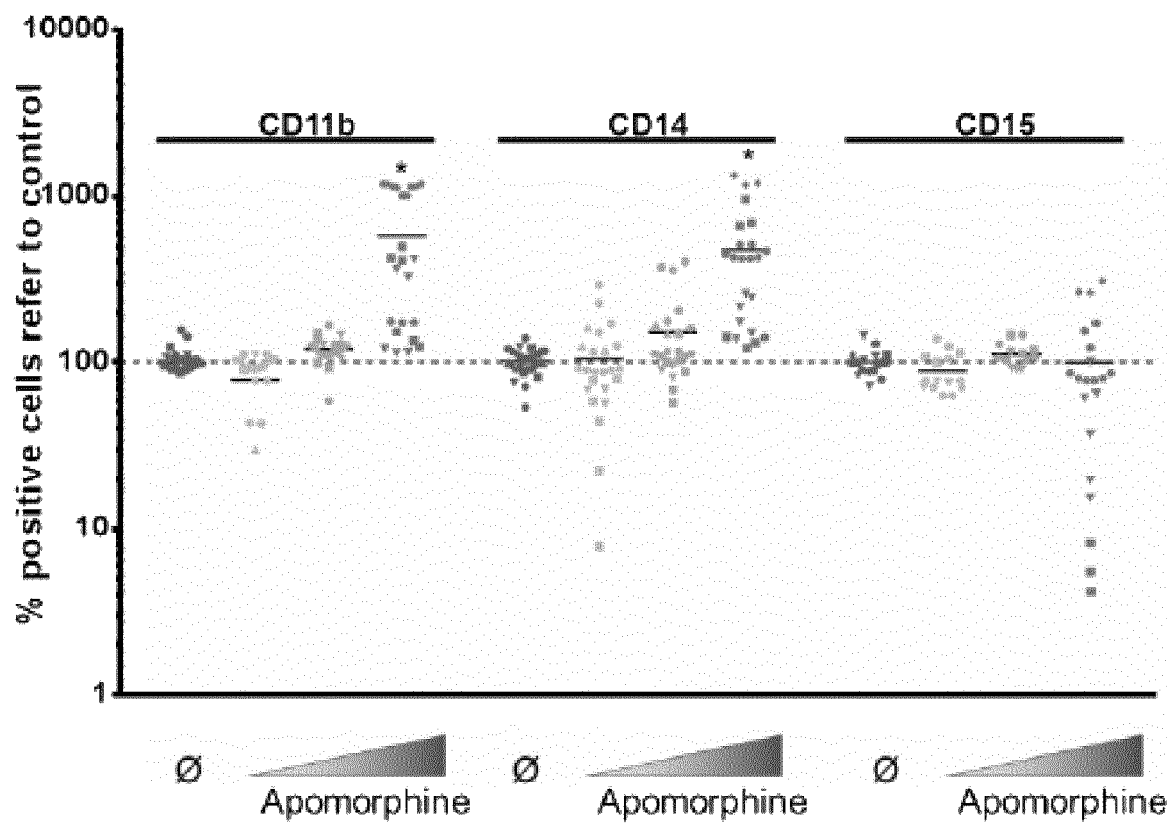
FIG. 6. 5HTR antagonist Apomorphine induced myeloid differentiation on primary patient AML samples. $5\times10^6$ primary AML cells per mL were treated with Apomorphine at 0.1, 1 and 10 µM in complete IMDM media for 72 h at 37° C. and 5% $CO_2$. AML bulk population was identified based on their CD45 expression and SSC profile by cytometry. The surface expression of CD11b, CD14 and CD15 was detected by flow cytometry. Death cells were excluded by 7-AAD-positive staining. 9 primary AML samples were analyzed in triplicates. Each symbol represents a specific AML patient. Bars represent the cell viability mean of each replicate. $*p<0.05$.
Figure 7:
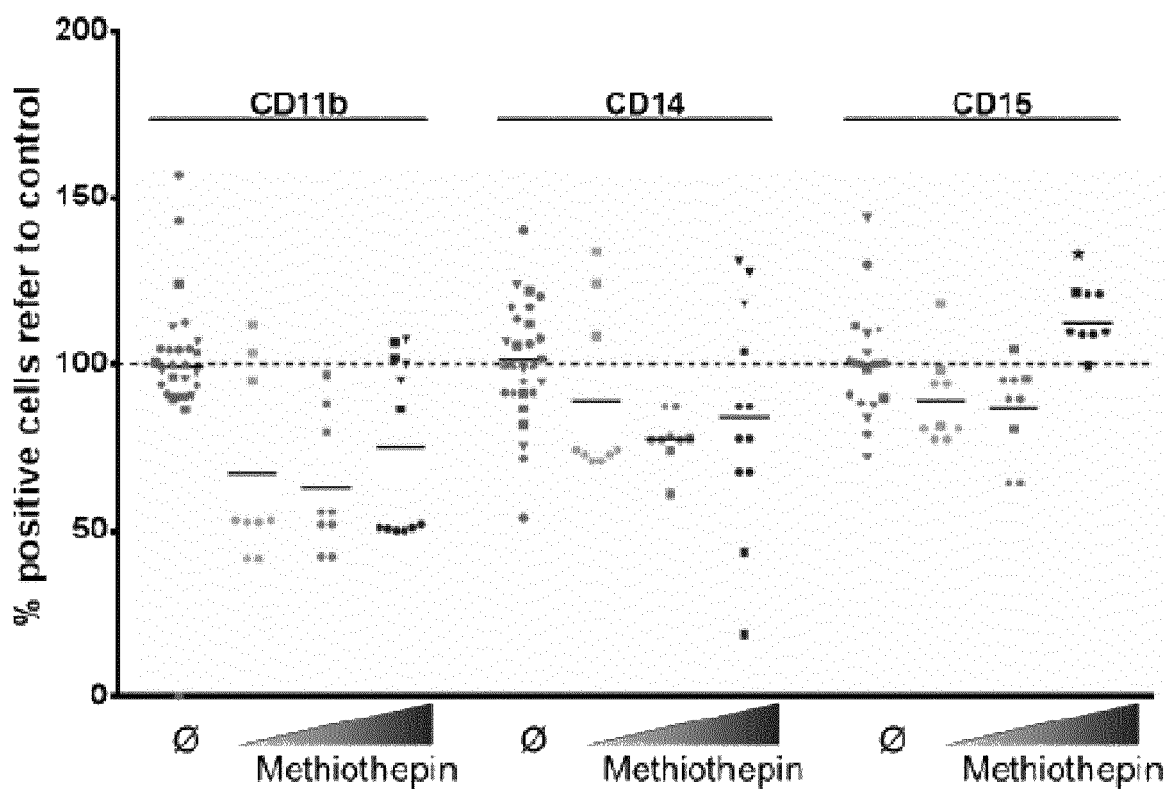
FIG. 7. 5HTR antagonist Methiothepin induced myeloid differentiation on primary patient AML samples. $5\times10^6$ primary AML cells per mL were treated with Methiothepin at 0.1, 1 and 10 µM in complete IMDM media for 72 h at 37° C. and 5% $CO_2$. AML bulk population was identified based on their CD45 expression and SSC profile by cytometry. The surface expression of CD11b, CD14 and CD15 was detected by flow cytometry. Death cells were excluded by 7-AAD-positive staining. 9 primary AML samples were analyzed in triplicates. Each symbol represents a specific AML patient. Lines represent the cell viability mean of each replicate. $*p<0.05$.

Similarly, Apomorphine and Methiothepin induced the upregulation of myeloid markers on primary AML patient samples (FIGS. 6 and 7).

Example 4

Figure 8:
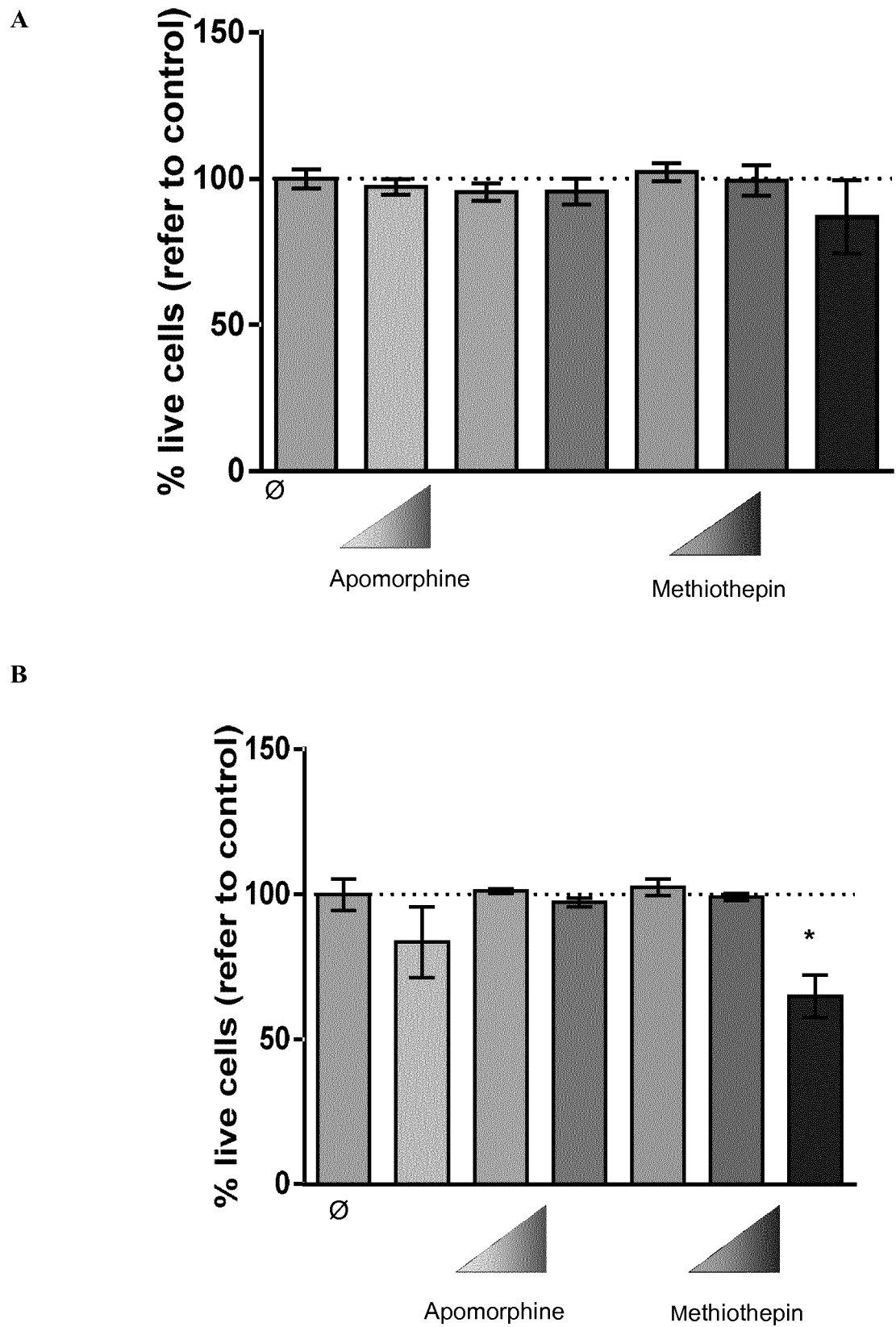
FIG. 8. Healthy blood cell viability remains unaffected after treatment with 5HTR antagonists. $5\times10^6$ ficoll-isolated mononuclear cells from peripheral blood samples obtained from healthy donors were treated with Apomorphine or Methiothepin at 0.1, 1 and 10 µM per 6 mL in complete RPMI media for 24 h (A) or 72 h (B) at 37° C. and 5% $CO_2$.

5HTR Antagonists have No Effect Neither on Healthy Blood Cells Nor on Healthy Haematopoietic Stem/Progenitor Cells Peripheral blood cells from healthy donors were isolated and treated with 5HTR antagonists using the same conditions as for primary patient AML samples. Unlike the latter, healthy blood cells remains unaffected upon treatment with Apomorphine or Methiothepin (FIG. 8).

To study the effect of 5HTR antagonist treatment on haematopoietic stem/progenitor cells, mononuclear cells from umbilical cord blood samples from healthy donors were isolated and the lineage-negative fraction was cultured in the presence of Apomorphine. Unlike AML cells, primary haematopoietic stem/progenitor cells remain unaffected upon treatment. No significant changes in cell viability were observed in the frequency of each population or the absolute number of cells (FIG. 9).

Example 5

5HTR Antagonists Reduce the Clonogenic Capacity of AML Blasts while Sparing Healthy Hematopoietic Stem Cells Taking into account that 5HTR antagonists reduced the cell viability of the most primitive AML population, the clonogenic capacity upon treatment was investigated. Primary patient AML samples were cultured in the presence of Apomorphine and Methiothepin for 18 h and plated in a semi-solid methylcellulose media for 14 days in the presence of instructive cytokines at a concentration of fifty thousand cells per mL. Colonies were counted by light microscopy based on morphology and cellularity. As shown in FIG. 10, both 5HTR antagonists reduced the clonogenic capacity of primary AML samples measured by the number of CFU-B obtained.

Next, lineage-depleted umbilical cord blood cells were treated with Apomorphine or Methiothepin as done above for AML cells. 14 days after plating, colonies were counted by light microscopy based on morphology and cellularity. None of the 5HTR antagonists affected the clonogenic capacity of healthy haematopoietic stem/progenitor cells as measured by either the total number of colonies or the frequency of each subtype of CFU (FIG. 11).

Example 6

5HTRs are Differentially Expressed on AML Patient Samples

To determine if 5HTRs are differentially expressed on AML patient samples versus healthy blood samples, their expression on primary patient AML peripheral blood samples, healthy donor peripheral blood samples and AML cell lines were studied by flow cytometry. As shown in FIG. 12, primary patient AML peripheral blood cells expressed 5HTRs in a significant higher quantity compared to healthy donors.

Example 7

5HTRs Expression Correlates with the Clinical Outcome in AML Patients

5HTR1A and 5HTR1B mRNA expression levels were determined in primary patient AML samples and correlated with the clinical outcome. Two patient groups were defined based on the cytogenetic risk: good (favorable molecular group) and bad (unfavorable molecular group). In both cases, there was an association between high expression of each 5HTR mRNA and worse clinical outcome (FIG. 13).

Example 8

Serotonin Receptor (5HTR) Antagonists Reduce the Clonogenic Capacity of AML Cells in Secondary CFUs In order to assay the clonogenic capacity in vitro, equivalent apomorphine-, methiothepin- and vehicle-treated primary CFU-Bs from AML patients (as explained in example 5) were serially plated in a semi-solid methylcellulose media for 14 days in the presence of instructive cytokines at a concentration of fifty thousand cells per mL but in the absence of any drug. Colonies were counted by light microscopy based on morphology and cellularity. As shown in FIG. 14, a reduction in the clonogenic capacity was observed upon treatment.

Example 9

Treatment with Serotonin Receptor Antagonists Reduced AML Burden in an In Vivo Xenotransplantation Mouse Model, Sparing Healthy Blood Cells Leukemia cells mainly reside in the bone marrow niche where the stroma cell compartment provides paracrine signaling that strongly mediates their survival and proliferation and protects them from apoptosis ( ). Accordingly, conditioned immunodeficient NOD.Cg-Prkdc$^{scid}$ Il2rg$^{tm1Wjl}$/SzJ (NSG) mice (Sanchez et al Leukemia. 2009 November; 23(11):2109-17) were transplanted with human AML cells and left for 7 days for the leukemia to be established. Afterwards, mice were treated every 2 days with a total of 4 intraperitoneal doses of apomorphine (5 mg/kg weight) (Schmidt et al J Neurosci. 1982 March; 2(3):376-80) or methiothepin (0.1 mg/kg weight) (Ginawi et al J Physiol Pharmacol. 2004 June; 55(2):357-69) for 7 days. Both 5HTR1 antagonists produced a significant reduction in AML burden in bone marrow (BM) as compared to vehicle-treated mice (FIG. 15).

Leukemia-initiating cells (LIC) or LSCs are responsible for the engraftment of AML cells in xenograft mouse models and are thought to initiate and maintain the disease in humans. Primary AML patient samples were treated ex vivo with 5HTR antagonists for 18 h and transplanted into conditioned immunodeficient NSG mice. Eight weeks after transplantation, murine bone marrow was analyzed for the presence of human AML cells. As shown in FIG. 16, apomorphine- and methiothepin-treated AML cells demonstrated less homing and engraftment capacity compared to vehicle-treated AML cells. Interestingly, a negligible effect was observed in the normal hematopoietic regeneration capacity of lineage-depleted UCB cells after treatment with apomorphine and methiothepin (FIG. 16).

In order to assay the in vivo self-renewal capacity remaining in the engrafted samples, secondary transplants were performed. Less than 35% of AML cells were detected in mice injected with apomorphine- or methiothepin-treated cells (FIG. 17). However, healthy hematopoietic stem cells retained their self-renewal and differentiation capacity upon treatment as shown by their regeneration potential in secondary transplants (FIG. 17). Moreover, the clonogenic capacity of engrafted samples was significantly reduced in AML cells treated with 5HTR1 antagonists as measured by CFU assays. Interestingly, little effect is observed in engrafted healthy HSCs (FIG. 17).

The invention claimed is:

1. A method of treating a subject suffering from acute myeloid leukemia (AML) comprising administering a type 1B serotonin receptor (5-HTR 1B) inhibitor to the subject if the AML cells express 5-HTR 1B, wherein the administration of the 5-HTR 1B inhibitor to the subject induces cell death in the AML cells.

* * * * *